United States Patent
Iimura et al.

(10) Patent No.: US 10,047,199 B2
(45) Date of Patent: Aug. 14, 2018

(54) COPOLYMER HAVING CARBOSILOXANE DENDRIMER STRUCTURE, AND COMPOSITION AND COSMETIC CONTAINING THE SAME

(75) Inventors: Tomohiro Iimura, Sodegaura (JP); Haruhiko Furukawa, Chiba (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

(21) Appl. No.: 13/517,279

(22) PCT Filed: Dec. 22, 2010

(86) PCT No.: PCT/JP2010/073861
§ 371 (c)(1),
(2), (4) Date: Jun. 20, 2012

(87) PCT Pub. No.: WO2011/078407
PCT Pub. Date: Jun. 30, 2011

(65) Prior Publication Data
US 2012/0263662 A1    Oct. 18, 2012

(30) Foreign Application Priority Data
Dec. 24, 2009  (JP) ................. 2009-293369

(51) Int. Cl.
| | | |
|---|---|---|
| *A61K 8/81* | (2006.01) | |
| *A61Q 1/00* | (2006.01) | |
| *A61Q 17/04* | (2006.01) | |
| *A61Q 1/06* | (2006.01) | |
| *A61Q 1/10* | (2006.01) | |
| *A61Q 15/00* | (2006.01) | |
| *C08F 230/08* | (2006.01) | |
| *A61Q 1/12* | (2006.01) | |
| *C08G 77/442* | (2006.01) | |
| *A61K 8/891* | (2006.01) | |
| *C08L 83/10* | (2006.01) | |
| *A61Q 1/02* | (2006.01) | |
| *A61Q 1/04* | (2006.01) | |

(52) U.S. Cl.
CPC ............ *C08G 77/442* (2013.01); *A61K 8/891* (2013.01); *A61Q 17/04* (2013.01); *C08L 83/10* (2013.01); *A61Q 1/02* (2013.01); *A61Q 1/04* (2013.01); *A61Q 1/06* (2013.01); *A61Q 1/10* (2013.01); *A61Q 1/12* (2013.01)

(58) Field of Classification Search
CPC .......... A61K 8/891; A61Q 17/04; A61Q 1/02; A61Q 1/04; A61Q 1/06; A61Q 1/10; A61Q 1/12; C08G 77/442; C08L 83/10
See application file for complete search history.

(56) References Cited

U.S. PATENT DOCUMENTS

| | | |
|---|---|---|
| 4,980,167 A | 12/1990 | Harashima et al. |
| 5,654,362 A | 8/1997 | Schulz, Jr. et al. |
| 5,939,478 A | 8/1999 | Beck et al. |
| 5,981,680 A | 11/1999 | Petroff et al. |
| 6,238,656 B1 | 5/2001 | Morita et al. |
| 6,238,745 B1 | 5/2001 | Morita et al. |
| 6,280,748 B1 | 8/2001 | Morita et al. |
| 6,291,021 B1 | 9/2001 | Morita et al. |
| 6,306,992 B1 | 10/2001 | Yoshitake et al. |
| 6,420,504 B1 | 7/2002 | Yoshitake et al. |
| 6,534,590 B1 | 3/2003 | Aso et al. |
| 6,602,949 B2 | 8/2003 | Furukawa et al. |
| 7,244,439 B2 | 7/2007 | Yago et al. |
| 7,482,419 B2 | 1/2009 | Caprasse et al. |
| 8,034,891 B2 | 10/2011 | Okawa |
| 2004/0156809 A1 | 8/2004 | Ono et al. |
| 2005/0008597 A1 | 1/2005 | Furukawa et al. |
| 2006/0193803 A1* | 8/2006 | Farcet ............. A61K 8/31 424/70.1 |
| 2008/0003195 A1 | 1/2008 | Arnaud et al. |

(Continued)

FOREIGN PATENT DOCUMENTS

| | | |
|---|---|---|
| CN | 101084863 A | 12/2007 |
| CN | 101472979 A | 7/2009 |
| EP | 0963751 A2 | 12/1999 |

(Continued)

OTHER PUBLICATIONS

English language abstract and translation for JP 2704730 extracted from the espacenet.com and PAJ databases on Aug. 17, 2012, 30 pages.
English language abstract for JP 2-243612 extracted from the espacenet.com database on Aug. 17, 2012, 10 pages.
English language abstract and translation for JP 05-237360 extracted from the PAJ database on Aug. 20, 2012, 44 pages.
English language abstract and translation for JP 07-196946 extracted from the PAJ database on Aug. 20, 2012, 38 pages.
English language abstract and translation for JP 08-012524 extracted from the PAJ database on Aug. 17, 2012, 28 pages.
English language abstract and translation for JP 08-012545 extracted from the PAJ database on Aug. 17, 2012, 27 pages.
English language abstract and translation for JP 08-012546 extracted from the PAJ database on Aug. 17, 2012, 26 pages.

(Continued)

*Primary Examiner* — Matthew P Coughlin
*Assistant Examiner* — Thurman M Wheeler
(74) *Attorney, Agent, or Firm* — Howard & Howard Attorneys PLLC

(57) ABSTRACT

The present invention relates to a copolymer having a specified carbosiloxane dendrimer structure and a long-chain alkyl group with 14 to 22 carbon atoms in a specified ratio, and a cosmetic comprising the copolymer as a cosmetic raw material. The cosmetic raw material has good miscibility with other cosmetic raw materials, and therefore, can improve stability of the formulation in a cosmetic, as well as can provide good water resistance, sebum resistance, glossiness, tactile sensation and/or adhesive properties to the hair and/or skin to a cosmetic, and also provide a cosmetic formed by blending the aforementioned cosmetic raw material, which exhibits superior surface protective properties, outer appearance and/or sensation during use.

20 Claims, No Drawings

(56) References Cited

U.S. PATENT DOCUMENTS

2008/0269358 A1 10/2008 Inoue et al.
2011/0110995 A1 5/2011 Hasegawa et al.

FOREIGN PATENT DOCUMENTS

| EP | 1055674 A1 | 11/2000 |
|---|---|---|
| JP | 2-243612 A | 9/1990 |
| JP | 05-237360 A | 9/1993 |
| JP | 07-196946 A | 8/1995 |
| JP | 08-012524 A | 1/1996 |
| JP | 08-012545 A | 1/1996 |
| JP | 08-012546 A | 1/1996 |
| JP | 09-171154 A | 6/1997 |
| JP | 09-241511 A | 9/1997 |
| JP | 2704730 B2 | 1/1998 |
| JP | 10-036219 A | 2/1998 |
| JP | 11-001530 A | 1/1999 |
| JP | 11-193331 A | 7/1999 |
| JP | 2000-063225 A | 2/2000 |
| JP | 2000-119139 A | 4/2000 |
| JP | 2000-226551 A | 8/2000 |
| JP | 2000-281523 A | 10/2000 |
| JP | 2003-226611 A | 8/2003 |
| JP | 2007-532754 A | 11/2007 |
| WO | WO 02/100356 A1 | 12/2002 |
| WO | WO 2006/106728 A1 | 10/2006 |
| WO | WO2008072716 * | 6/2008 |
| WO | WO 2009/142047 A1 | 11/2009 |
| WO | WO 2011/078408 A1 | 6/2011 |

OTHER PUBLICATIONS

English language abstract and translation for JP 09-171154 extracted from the PAJ database on Aug. 17, 2012, 36 pages.
English language abstract and translation for JP 09-241511 extracted from the PAJ database on Aug. 17, 2012, 29 pages.
English language abstract and translation for JP 10-036219 extracted from the PAJ database on Aug. 20, 2012, 37 pages.
English language abstract and translation for JP 11-001530 extracted from the PAJ database on Aug. 17, 2012, 47 pages.
English language abstract for JP 11-193331 extracted from the espacenet.com database on Aug. 20, 2012, 15 pages.
English language abstract and translation for JP 2000-063225 extracted from the PAJ database on Aug. 17, 2012, 61 pages.
English language abstract and translation for JP 2000-119139 extracted from the PAJ database on Aug. 17, 2012, 30 pages.
English language abstract for JP 2000-281523 extracted from the espacenet.com database on Aug. 20, 2012, 24 pages.
English language abstract for JP 2003-226611 extracted from the espacenet.com database on Aug. 17, 2012, 19 pages.
English language abstract not available for JP 2007-532754; However, see English language equivalent U.S. Pat. No. 7,482,419. Original Document extracted from the espacenet.com database on Aug. 20, 2012, 39 pages.
English language abstract for WO 02/100356 extracted from the espacenet.com database on Aug. 21, 2012, 71 pages.
International Search Report for Application No. PCT/JP2010/073861 dated May 26, 2011, 3 pages.
International Search Report for Application No. PCT/JP2010/073862 dated May 26, 2011, 3 pages.
English language abstract for CN 101084863 extracted from the espacenet.com database on May 23, 2013, 55 pages.
English language abstract for CN 101472979 extracted from the espacenet.com database on Oct. 4, 2013, 126 pages.
Shin-Etsu Technical Data Sheet for KF-9909 (Accessed on Aug. 20, 2013), pp. 1-2, http://www.silicone.jp/e/products/personalcare/pdf/KF/KF-9909.pdf).
English language abstract for WO 2006/106728 extracted from espacenet.com database on Dec. 15, 2014, 2 pages.
"Clearco Product Information for decamethylcyclopentasiloxane" (http://www.clearcoproducts.com/pdf/cosmetic/np-cyclo-2345.pdf), accessed on Sep. 30, 2014, 1 page.
English language abstract for JP 2000-226551 extracted from espacenet.com database on Nov. 3, 2014, 2 pages (English language equivalent U.S. Pat. No. 6,291,021 previously submitted on Oct. 18, 2013).
English language abstract for WO 2009/142047 extracted from espacenet.com database on Nov. 3, 2014, 2 pages.

\* cited by examiner

COPOLYMER HAVING CARBOSILOXANE DENDRIMER STRUCTURE, AND COMPOSITION AND COSMETIC CONTAINING THE SAME

TECHNICAL FIELD

The present invention relates to a cosmetic, and in particular, relates to a novel copolymer having a specified carbosiloxane dendrimer structure, as well as a composition and a cosmetic containing the same.

This application claims priority to and all the advantages of International Patent Application No. PCT/JP2010/073861, filed on Dec. 22, 2010, which claims priority to Japanese Patent Application No. JP 2009-293369, filed on Dec. 24, 2009.

BACKGROUND ART

Heretofore, it is known that a copolymer of an organopolysiloxane with a radical-polymerizable group and a radical-polymerizable monomer is blended as a film-forming agent for use in a cosmetic. For example, Japanese Patent No. 2704730 proposes that a vinyl-based polymer obtained by copolymerizing dimethylpolysiloxane containing a radical-polymerizable group at one terminal with various types of alkyl acrylates is blended in a cosmetic. The aforementioned vinyl-based polymers provide water repellency and smoothness to a cosmetic. On the other hand, there are disadvantages in that poor miscibility with other cosmetic raw materials is exhibited since a linear silicone is grafted, and therefore, poor stability in blending in a cosmetic is exhibited, as well as a film formed therefrom fails to have sufficient sebum resistance and adhesive properties with respect to hair and skin.

In order to solve the problems described above, a cosmetic raw material containing a vinyl-based polymer having a carbosiloxane dendrimer structure, or containing both a carbosiloxane dendrimer structure and a fluorinated organic group, as a main component has been suggested (see Japanese Unexamined Patent Application, First Publication No. 2000-63225; and Japanese Unexamined Patent Application First Publication No. 2003-226611). Even in the case of using the aforementioned vinyl-based polymers, sufficiently satisfied water resistance, sebum resistance and the like cannot be exhibited, and in particular, sufficient glossiness cannot be provided on a film formed therefrom.

On the other hand, Japanese Unexamined Patent Application, First Publication No. 2000-119139 proposes a vinyl-based polymer between a dimethylpolysiloxane containing a radical-polymerizable group at one terminal and an alkyl acrylate monomer containing a long-chain alkyl group with 16 to 22 carbon atoms. The aforementioned vinyl-based copolymer is superior with respect to the copolymers described in Japanese Patent No. 2704730, but has problems such as poor sebum resistance and the like, and further improvements thereon are needed.

DISCLOSURE OF INVENTION

Technical Problems

In view of the aforementioned circumstances of the prior art, the present invention has been made. An objective of the present invention is to provide a cosmetic raw material which has good miscibility with other cosmetic raw materials, and therefore, can improve the stability of the formulation in a cosmetic, as well as can provide good water resistance, sebum resistance, glossiness, tactile sensation and/or adhesive properties to the hair and/or skin to a cosmetic, and also provide a cosmetic formed by blending the aforementioned cosmetic raw material, which exhibits superior surface protective properties, outer appearance and/or sensation during use.

Technical Solution

The objective of the present invention can be achieved by a copolymer of, at least, (A) an unsaturated monomer having a carbosiloxane dendrimer structure presented by the following formula (1):

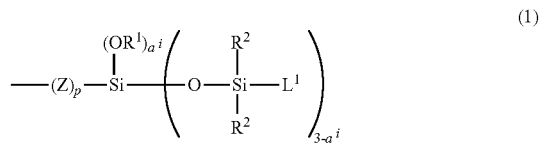

wherein

Z is a divalent organic group;

p is 0 or 1;

each of $R^1$ and $R^2$ independently represents an alkyl group, an aryl group or an aralkyl group, having 1 to 10 carbon atoms; and $L^1$ is a silylalkyl group, in the case of i=1, represented by the following formula (2):

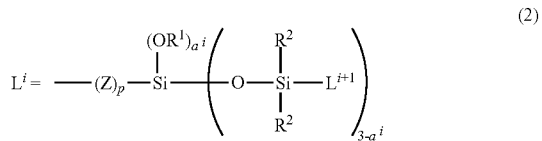

wherein

Z and p are the same as defined above;

$R^1$ and $R^2$ are the same as defined above;

i is an integer ranging from 1 to 10, which specifies the total number of generations of the aforementioned silylalkyl group;

$L^{i+1}$ is a group selected from the group consisting of a hydrogen atom, alkyl, aryl and aralkyl groups, having 1 to 10 carbon atoms and the aforementioned silylalkyl group, with the proviso that in the case of i=c, in which c is an integer ranging from 1 to 10 and specifies generation of the aforementioned silylalkyl group, $L^{i+1}$ is a hydrogen atom, or an alkyl, aryl or aralkyl group, having 1 to 10 carbon atoms; and in the case of i<c, $L^{i+1}$ is the aforementioned silylalkyl group; and $a^i$ is an integer ranging from 0 to 3, and (B) an unsaturated monomer having a long-chain alkyl group with 14 to 22 carbon atoms, with the proviso that {(weight of component (A))/(weight of all the monomers)}≥{(weight of component (B))/(weight of all the monomers)}.

The aforementioned unsaturated monomer having the carbosiloxane dendrimer structure (A) preferably has a group selected from the group consisting of an acryl or methacryl group-containing organic group represented by the following general formula:

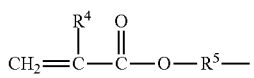

wherein $R^4$ is a hydrogen atom or a methyl group; and $R^5$ is an alkylene group having 1 to 10 carbon atoms, or

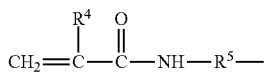

wherein $R^4$ and $R^5$ are the same as defined above, an alkenylaryl group-containing organic group represented by the following general formula:

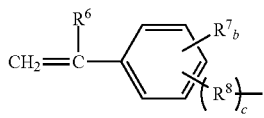

wherein $R^6$ is a hydrogen atom or a methyl group; $R^7$ is an alkyl group having 1 to 10 carbon atoms; $R^8$ is an alkylene group having 1 to 10 carbon atoms; b is an integer ranging from 0 to 4; and c is 0 or 1, and an alkenyl group having 2 to 10 carbon atoms.

The aforementioned unsaturated monomer having a long-chain alkyl group with 14 to 22 carbon atoms (B) is preferably a ($C_{14-22}$ alkyl) (meth)acrylate.

The copolymer of the present invention may be a copolymer obtained by copolymerizing the aforementioned components (A) and (B) and at least one type of unsaturated monomer having no long-chain alkyl groups with 14 to 22 carbon atoms.

In addition, the objective of the present invention can be achieved by a cosmetic comprising the aforementioned copolymer. Namely, the aforementioned copolymer can be extremely suitably employed as a cosmetic raw material used as a film-forming component of a cosmetic.

In addition, the copolymer of the present invention can be preferably blended in a cosmetic, in the form of a copolymer composition in which the copolymer is dispersed in or uniformly dissolved in an oil agent or agents. The cosmetic of the present invention can comprise an oil agent or agents derived from the aforementioned copolymer composition, and in addition, may be a cosmetic in which desirable oil agent(s) is/are separately blended in accordance with types or compositions of cosmetics.

The aforementioned oil agent can be a silicone oil, and the aforementioned silicone oil can be a hydrophobic silicone oil having a viscosity ranging from 0.65 to 100,000 $mm^2/s$ at 25° C.

In addition, the aforementioned silicone oil can be an organopolysiloxane represented by the following general formula (3), (4) or (5):

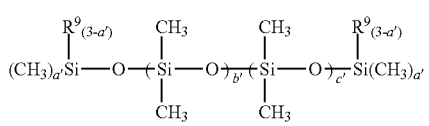

(3)

wherein
$R^9$ is a hydrogen atom, a hydroxyl group or a group selected from monovalent non-substituted or fluorine- or amino-substituted $C_{1-30}$ alkyl groups, aryl groups, alkoxy groups and groups represented by $(CH_3)_3SiO\{(CH_3)_2SiO\}_l Si(CH_3)_2CH_2CH_2-$,
wherein l is an integer ranging from 0 to 1,000;
a' is an integer ranging from 0 to 3;
b' is an integer ranging from 0 to 1,000; and
c' is an integer ranging from 0 to 1,000, with the proviso that $1 \le b'+c' \le 2,000$,

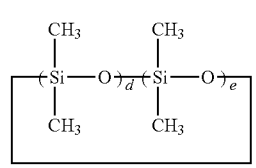

(4)

wherein
$R^9$ is the same as defined above;
d is an integer ranging from 0 to 8; and
e is an integer ranging from 0 to 8, with the proviso that $3 \le d+e \le 8$,

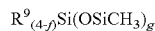

(5)

wherein
$R^9$ is the same as defined above;
f is an integer ranging from 1 to 4; and
g is an integer ranging from 0 to 500.

The cosmetic of the present invention can further comprise at least one surfactant selected from the group consisting of anionic surfactants, cationic surfactants, nonionic surfactants, amphoteric surfactants and semi-polar surfactants.

The cosmetic of the present invention can further comprise at least one powder and/or at least one coloring agent. The aforementioned powder can be selected from the group consisting of inorganic pigment powders, organic pigment powders and resin powders, having an average particle size ranging from 1 nm to 20 μm. At least one part of the aforementioned powder and/or the aforementioned coloring agents may be subjected to a water-repellent treatment.

The cosmetic of the present invention can further comprise at least one selected from the group consisting of water-soluble polymers, oil-soluble gelling agents and organo-modified-clay minerals.

The cosmetic of the present invention can further comprise at least one selected from the group consisting of silicone resins, silicone elastomers and organo-modified silicones.

The cosmetic of the present invention can further comprise at least one UV-ray protective component.

The present invention also relates to a skin care product, a hair product, an antiperspirant product, a deodorant product, a makeup product or a UV-ray protective product, containing the aforementioned cosmetic.

Advantageous Effects of Invention

In the copolymer of the present invention, a silicone which is not linear, but is in the form of a highly branched dendrimer is grafted on a main chain, and a long-chain alkyl group is also grafted on the main chain. For this reason, the copolymer exhibits good miscibility with other various cosmetic raw materials. Therefore, superior stability of the formulation in a cosmetic can be exhibited. In addition, the copolymer of the present invention can provide good water resistance, sebum resistance, glossiness, tactile sensation, and/or adhesive properties to the hair and/or skin to a cosmetic. In addition, in the copolymer of the present invention, the grafting amount of the carbosiloxane dendrimer is equivalent to or more than the grafting amount of the long-chain alkyl chain. For this reason, a film having particularly superior properties in view of sebum resistance and glossiness can be formed. In addition, in the copolymer of the present invention, at least two types of hydrophobic functional groups described above are grafted, and thereby, the copolymer possesses advantages in that superior miscibility with various oil agents is exhibited, and the copolymer can be stably blended in a cosmetic as a composition with oil agents.

The cosmetic of the present invention comprises the aforementioned copolymer. For this reason, superior surface protective properties in view of water resistance, sebum resistance, glossiness, tactile sensation, and/or adhesive properties with respect to the hair and/or skin, as well as superior outer appearance and/or a superior sensation during use can be provided.

BEST MODES FOR CARRYING OUT THE INVENTION

The copolymer of the present invention has, at least, a carbosiloxane dendrimer structure represented by the following formula (1):

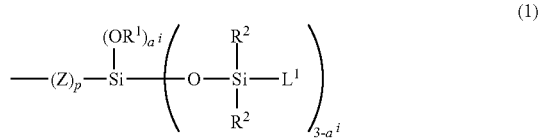
(1)

wherein
Z is a divalent organic group;
p is 0 or 1;
each of $R^1$ and $R^2$ independently represents an alkyl, aryl or aralkyl group, having 1 to 10 carbon atoms; and
$L^1$ is a silylalkyl group, in the case of i=1, represented by the following formula (2):

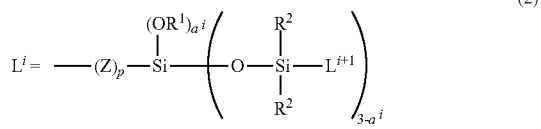
(2)

wherein
Z and p are the same as defined above;
$R^1$ and $R^2$ are the same as defined above;
i is an integer ranging from 1 to 10, preferable ranging from 1 to 5, more preferably ranging from 1 to 3 and is further preferably 1 or 2, which specifies the total number of generations of the aforementioned silylalkyl group;
$L^{i+1}$ is a group selected from the group consisting of a hydrogen atom, alkyl, aryl and aralkyl groups, having 1 to 10 carbon atoms and the aforementioned silylalkyl group, with the proviso that in the case of i=c in which c is an integer ranging from 1 to 10, preferably ranging from 1 to 5, more preferably ranging from 1 to 3 and being further preferably 1 or 2, and specifying generation of the aforementioned silylalkyl group, $L^{i+1}$ is a hydrogen atom, an alkyl, aryl or aralkyl group, having 1 to 10 carbon atoms;
and in the case of i<c, $L^{i+1}$ is the aforementioned silylalkyl group; and
$a^i$ is an integer ranging from 0 to 3, preferably ranging from 0 to 2, more preferably ranging from 0 to 1 and being further preferably 0, and
a long-chain alkyl group with 14 to 22 carbon atoms. The copolymer of the present invention preferably has a vinyl polymerization unit as a main chain, and has a carbosiloxane dendrimer structure and a structure in which a long-chain alkyl group with 14 to 22 carbon atoms is present at a side chain, with the proviso that the grafting amount (number) of the aforementioned carbosiloxane dendrimer structure is equivalent to or more than the grafting amount (number) of the aforementioned long-chain alkyl group.

Therefore, the copolymer of the present invention is a copolymer of an unsaturated monomer having the aforementioned carbosiloxane dendrimer structure (A) and an unsaturated monomer having the aforementioned long-chain alkyl group (B), with the proviso that {(weight of component (A))/(weight of all the monomers)}≥{(weight of component (B))/(weight of all the monomers)}. The ratio of (weight of component (A))/(weight of all the monomers) preferably ranges from 0.4 to 0.9, and more preferably ranges from 0.5 to 0.8. The ratio of (weight of component (B))/(weight of all the monomers) preferably 0.1 or more, but less than 0.4, preferably ranges from 0.1 to 0.3, and more preferably ranges from 0.1 to 0.2.

The divalent organic group is not particularly restricted, and examples thereof include, for example, a substituted or non-substituted, and linear or branched divalent hydrocarbon group having 1 to 30 carbon atoms. As examples of the substituted or non-substituted, and linear or branched divalent hydrocarbon group having 1 to 30 carbon atoms, mention may be made of, for example, linear or branched alkylene groups having 1 to 30 carbon atoms such as a methylene group, a dimethylene group, a trimethylene group, a tetramethylene group, a pentamethylene group, a hexamethylene group, a heptamethylene group, an octamethylene group and the like; alkenylene groups having 2 to 30 carbon atoms such as a vinylene group, an allylene group, a butenylene group, a hexenylene group, an octenylene group and the like; arylene groups having 6 to 30 carbon atoms such as a phenylene group, a diphenylene group and the like; alkylenearylene groups having 7 to 30 carbon atoms such as a dimethylenephenylene group and the like; and substituted groups thereof in which hydrogen atoms bonded to carbon atoms of the aforementioned groups are at least partially substituted by a halogen atom such as a fluorine atom or the like, or an organic group containing a carbinol group, an epoxy group, a glycidyl group, an acyl group, a carboxyl group, an amino group, a methacryl group, a mercapto group, an amide group, an oxyalkylene group or the like. The divalent hydrocarbon group is preferably a non-substituted divalent saturated hydrocarbon group having 1 to 30 carbon atoms, more preferably a linear or branched alkylene group having 1 to 6 carbon atoms, and in particular, preferably a dimethylene group.

For example, the divalent organic group may be a group selected from the following groups:

—R³—

—R³—CO—

—R³—COO—R³—

—CO—R³—

—R³—COO—R³'—

—R³—CONH—R³'—

—R³—R³'— wherein
R³ is the aforementioned substituted or non-substituted, and linear or branched divalent hydrocarbon group having 1 to 30 carbon atoms, which may have a substituent as described above; and
R³' is a group selected from the following groups:

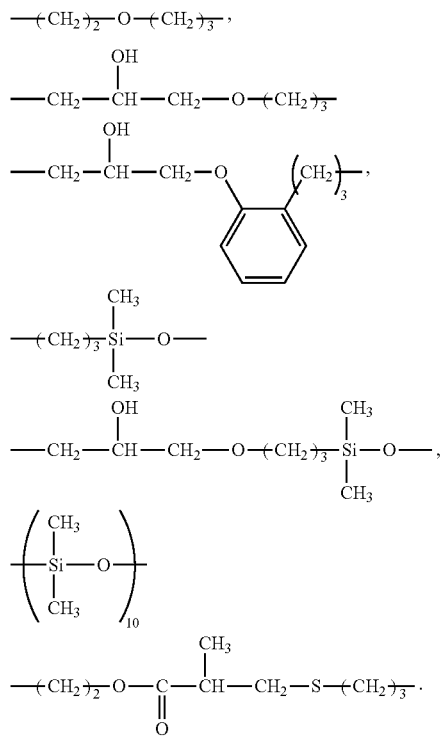

A divalent organic group represented by the following general formula: —R³— or —R³—R³'— which is derivable by means of a reaction between a hydrogen atom bonded to a silicon atom and an alkenyl group is preferred.
In the same manner as described above, a divalent organic group represented by the following general formula: —R³—COO—R³— or —R³—COO—R³'— which is derivable by means of a reaction between a hydrogen atom bonded to a silicon atom and an unsaturated carboxylic acid functional group is also preferred.

In particular, the aforementioned Z is preferably a linear or branched alkylene group having 1 to 30 carbon atoms, and particularly preferably a dimethylene group (ethylene group).

As examples of alkyl groups, aryl groups, or aralkyl groups, having 1 to 10 carbon atoms, mention may be made of, for example, linear or branched alkyl groups having 1 to 10 carbon atoms such, as a methyl group, an ethyl group, a propyl group, a butyl group, a pentyl group, a hexyl group, a heptyl group, an octyl group and the like; cycloalkyl groups having 3 to 10 carbon atoms such as a cyclopentyl group, a cyclohexyl group and the like; aryl groups having 6 to 10 carbon atoms such as a phenyl group, a tolyl group, a xylyl group and the like; aralkyl groups having 7 to 10 carbon atoms such as a benzyl group and the like; and substituted groups thereof in which hydrogen atoms bonded to carbon atoms of the aforementioned groups are at least partially substituted by a halogen atom such as a fluorine atom or the like, or an organic group containing a carbinol group, an epoxy group, a glycidyl group, an acyl group, a carboxyl group, an amino group, a methacryl group, a mercapto group, an amide group, an oxyalkylene group or the like. The alkyl group, aryl group or aralkyl group is preferably an unsubstituted alkyl, aryl or aralkyl group, having 1 to 10 carbon atoms, more preferably an unsubstituted alkyl or aryl group, having 1 to 6 carbon atoms, and in particular, preferably a methyl group, an ethyl group or a phenyl group.

The aforementioned carbosiloxane dendrimer structure is a chemical structure radially and highly branched from one silicon atom. The aforementioned "i" specifying the total number of generations of the aforementioned silylalkyl group indicates the degree of branching. For example, in the case in which the total number of generations i is 1 and $L^{i+1}$ is, for example, a methyl group, the aforementioned carbosiloxane dendrimer structure means the following structure.

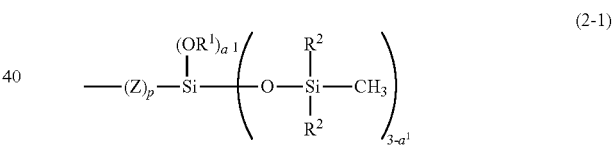

(2-1)

wherein Z, p, R¹ and R² are the same as defined above; and $a^i$ is an integer ranging from 0 to 3.

In the same manner as described above, in the case in which the generation i is 2 and $L^{i+1}$ is, for example a methyl group, the aforementioned carbosiloxane dendrimer structure means the following structure, wherein p=1.

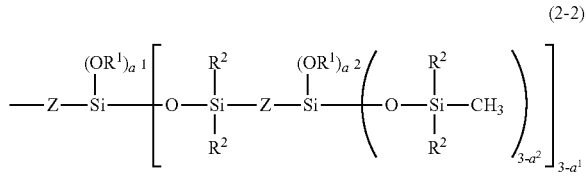

(2-2)

wherein Z, R¹ and R² are the same as defined above; and a¹ and a² indicate an integer ranging from 0 to 3.

In addition, in the case in which the generation i is 3 and $L^{i+1}$ is, for example, a methyl group, the aforementioned carbosiloxane dendrimer structure means the following structure wherein p=1.

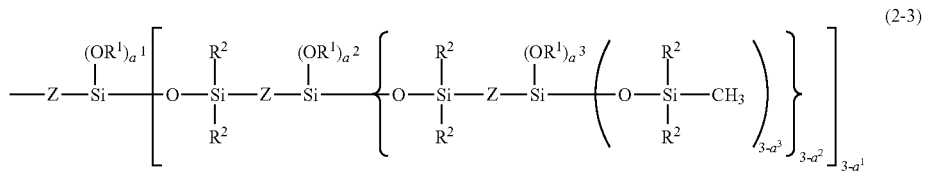

wherein Z, $R^1$ and $R^2$ are the same as defined above; and $a^1$, $a^2$ and $a^3$ indicate an integer ranging from 0 to 3.

As the aforementioned carbosiloxane dendrimer structures, in particular, the following structures are preferred.

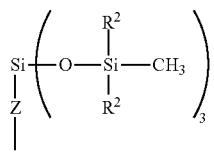

wherein Z and $R^2$ are the same as defined above.

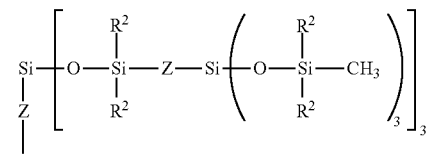

wherein Z and $R^2$ are the same as defined above.

The silylalkyl group having the aforementioned carbosiloxane dendrimer structure has a structure in which the carbosiloxane units are extended in the form of a dendrimer. For this reason, the aforementioned silylalkyl group is a functional group exhibiting increased water repellency (increased water resistance), as compared to linear or simply branched polysiloxane units. In addition, the aforementioned silylalkyl group having the carbosiloxane dendrimer structure is chemically stable, and for this reason, the silylalkyl group is a functional group providing advantageous properties such as usability in combination with various types of raw materials for use in cosmetics.

The aforementioned unsaturated monomer having the carbosiloxane dendrimer structure (A) is represented by, for example, the following formula (1'):

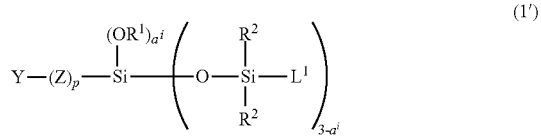

wherein
Y is a radically-polymerizable unsaturation-containing group; and
Z, p, $R^1$, $R^2$, $L^1$ and $a^i$ are the same as defined above.

The aforementioned unsaturation-containing group is not particularly restricted as long as the group has a radically polymerizable unsaturation. As examples thereof, mention may be made of, for example, a vinyl group, an allyl group, a (meth)acryl group and the like.

The aforementioned unsaturated monomer having the carbosiloxane dendrimer structure (A) preferably has a group selected from the group consisting of an acryl or methacryl group-containing organic group represented by the following general formula:

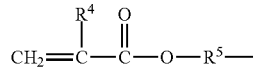

wherein $R^4$ is a hydrogen atom or a methyl group; and $R^5$ is an alkylene group having 1 to 10 carbon atoms, or

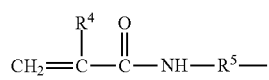

wherein $R^4$ and $R^5$ are the same as defined above, an alkenylaryl group-containing organic group represented by the following general formula:

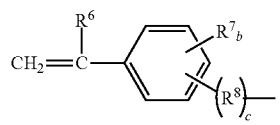

wherein $R^6$ is a hydrogen atom or a methyl group; $R^7$ is an alkyl group having 1 to 10 carbon atoms; $R^8$ is an alkylene group having 1 to 10 carbon atoms; b is an integer ranging from 0 to 4; and c is 0 or 1,
and an alkenyl group having 2 to 10 carbon atoms.

As examples of the aforementioned unsaturated monomers having the carbosiloxane dendrimer structure (A), mention may be made of, for example, those represented by the following formulae:

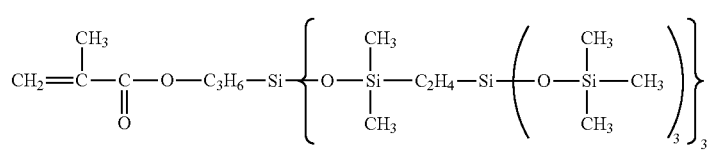

-continued
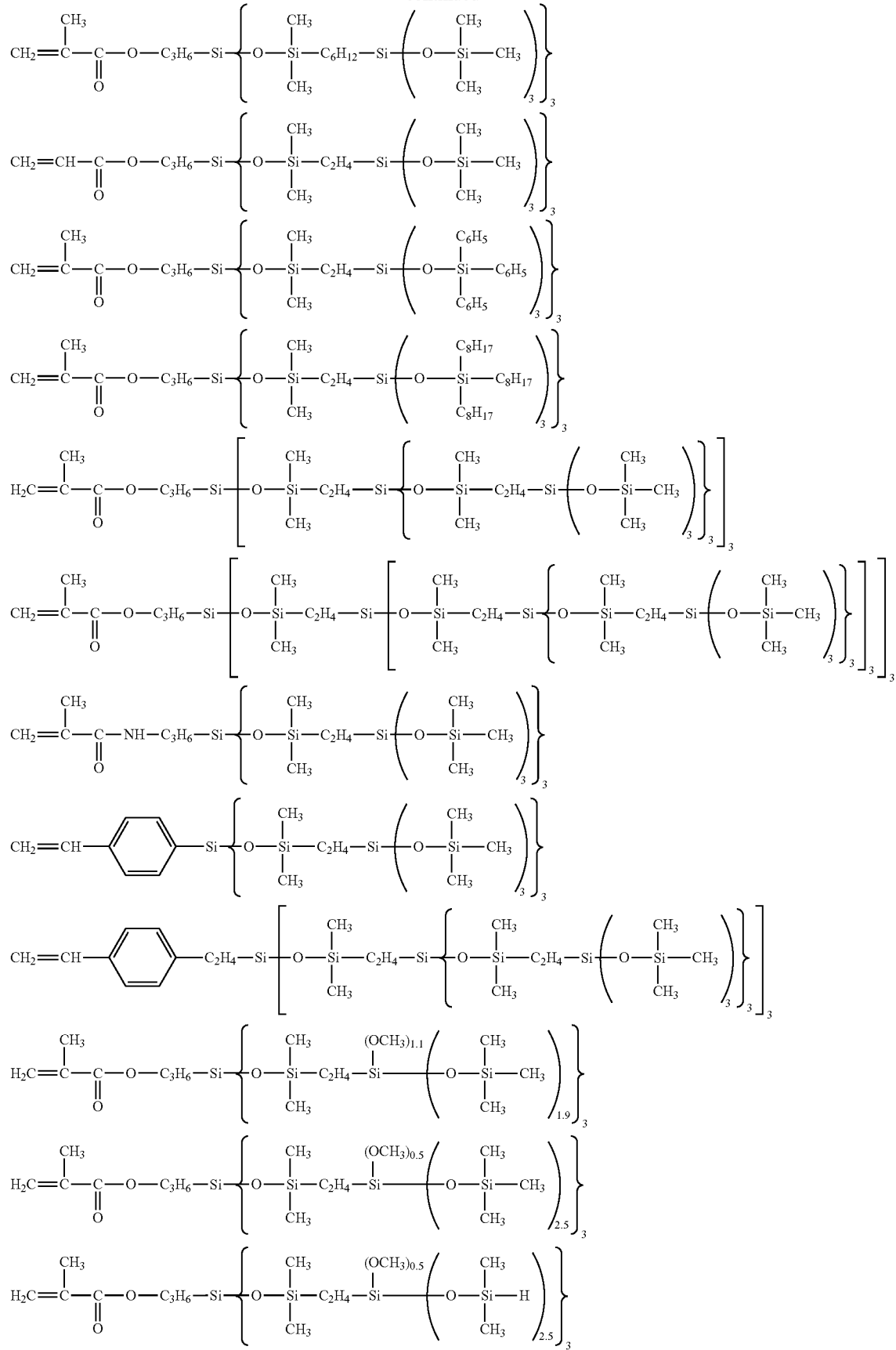

-continued

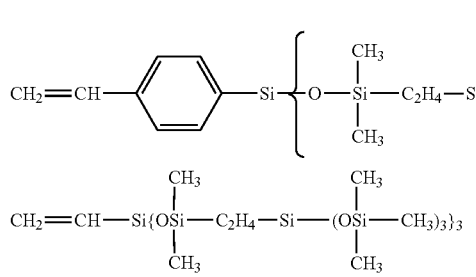 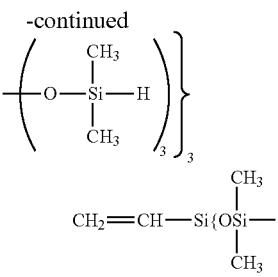

The aforementioned unsaturated monomer having the carbosiloxane dendrimer structure (A) can be produced in accordance with, for example, a method for producing a branched siloxane/silalkylene copolymer described in Japanese Unexamined Patent Application, First Publication No. H11-1530 (Japanese Patent Application No. H09-171154). For example, a silicon compound containing hydrogen atoms bonded to silicon atoms represented by the following general formula:

$$Y-Si-(OSiR^2_2H)_3$$

wherein Y and $R^2$ are the same as defined above, and an alkenyl group-containing organic silicon compound are subjected to a hydrosilylation reaction. As the silicon compound represented by the aforementioned formula, for example, 3-methacryloxypropyl tris(dimethylsiloxy)silane, 3-acryloxypropyl tris(dimethylsiloxy)silane, or 4-vinylphenyl tris(dimethylsiloxy)silane is used. As the organic silicon compound containing an alkenyl group, for example, vinyl tris(trimethylsiloxy)silane, vinyl tris(dimethylphenylsiloxy)silane, or 5-hexenyl tris(trimethylsiloxy)silane is used. The aforementioned hydrosilylation reaction is preferably carried out in the presence of a transition metal catalyst such as chloroplatinic acid, a platinum-vinylsiloxane complex or the like.

The aforementioned unsaturated monomer having a long-chain alkyl group (B) is a component for grafting a long-chain alkyl group to the main chain of the copolymer, in addition to the aforementioned silylalkyl group having the carbosiloxane dendrimer structure in the copolymer of the present invention. The copolymer of the present invention possesses the long-chain alkyl group derived from the aforementioned component (B). For this reason, the copolymer of the present invention exhibits improved miscibility with various other cosmetic raw materials and in particular, an oil agent, as compared with a copolymer having only a silylalkyl group. Therefore, stability of the formulation in a cosmetic and the sensation during use thereof can be improved. The aforementioned component (B) is not particularly restricted as long as the component has the long-chain alkyl group having 14 to 22 carbon atoms and the radically-polymerizable unsaturation-containing group. Here, in view of sensation during use and formulation stability as cosmetic raw materials, the long-chain alkyl group of the aforementioned component (B) is an alkyl group preferably having 15 to 22 carbon atoms, more preferably having 16 to 22 carbon atoms, further more preferably having 17 to 22 carbon atoms, and most preferably having 18 to 22 carbon atoms. The long-chain alkyl group may be either one of a non-substituted long-chain alkyl group or a substituted long-chain alkyl group in which hydrogen atoms bonded to the carbon atoms thereof are at least partially substituted by a halogen atom such as a fluorine atom or the like, or an organic group containing a carbinol group, an epoxy group, a glycidyl group, an acyl group, a carboxyl group, an amino group, a methacryl group, a mercapto group, an amide group, an oxyalkylene group or the like. The long-chain alkyl group having 14 to 22 carbon atoms is not particularly restricted, and examples thereof may include, for example, a myristyl group, a palmityl group, a stearyl group, an isostearyl group, a behenyl group and the like. The aforementioned long-chain alkyl groups exhibit superior affinity with, in particular, hydrophobic alkyl groups contained in hydrocarbon-based oil agents or fatty acid ester-based oil agents, and possess advantages of improving the sensation during use and formulation stability of the cosmetics.

As examples of radically-polymerizable unsaturation-containing groups, mention may be made of groups derived from monovalent unsaturated carboxylic acids, or monovalent hydrocarbon groups having a carbon-carbon double bond at the molecular terminal as the unsaturation bond. For example, a vinyl group, an allyl group, a (meth)acryl group, a (meth)acryloxy group and the like may be mentioned.

The aforementioned unsaturated monomer having a long-chain alkyl group with 14 to 22 carbon atoms (B) is preferably a $C_{14-22}$ alkyl acrylate or a $C_{14-22}$ alkyl (meth) acrylate. As examples of the $C_{14-22}$ alkyl acrylates, mention may be made of myristyl acrylate, palmityl acrylate, stearyl acrylate, and behenyl acrylate. As examples of the $C_{14-22}$ alkyl(meth)acrylates, mention may be made of, for example, myristyl(meth)acrylate, palmityl(meth)acrylate, stearyl (meth)acrylate, behenyl(meth)acrylate and the like. The aforementioned unsaturated monomers may be used alone or in combination of two or more types thereof. For the functional purpose of improving miscibility with a specified oil agent and the like, two or more types of long-chain alkyl groups can be grafted on the main chain.

The copolymer of the present invention can be synthesized by copolymerizing at least the aforementioned unsaturated monomer having the carbosiloxane dendrimer structure (A) and the aforementioned unsaturated monomer having the long-chain alkyl group (B), with the proviso that the copolymer of the present invention is polymerized under the condition of {(weight of component (A))/(weight of all the monomers)}≥{(weight of component (B))/(weight of all the monomers)}. More particularly, the ratio of (weight of component (A))/(weight of all the monomers) preferably ranges from 0.3 to 0.9, and more preferably ranges from 0.35 to 0.65. The ratio of (weight of component (B))/(weight of all the monomers) is preferably 0.02 or more, but less than 0.5, and more preferably ranges from 0.05 to 0.4, and in particular, preferably ranges from 0.10 to 0.4. If the usage amount of the aforementioned component (A) is below the usage amount of the aforementioned component (B), the properties derived from the silylalkyl group having the carbosiloxane dendrimer structure may not be sufficiently provided to the copolymer in some cases. On the other hand, if the usage amount of the aforementioned component (B) is below the aforementioned lower limit, advantageous properties of the copolymer of the present invention such as miscibility with the cosmetic components on the basis of the structure in which both the silylalkyl group having the carbosiloxane dendrimer structure and the long-chain alkyl group are grafted on the main chain, that is the characteristic of the present invention, may not be sufficiently exhibited in some cases.

In addition to the aforementioned components (A) and (B), at least one unsaturated monomer having no long-chain alkyl group with 14 to 22 carbon atoms (C) may be copolymerized. In the present invention, the aforementioned unsaturated monomer of component (C) may be a mixture of two or more types of monomers. For the purpose of imparting functionabilities of the copolymer, a molecular design in which different types of functional groups are grafted on the main chain can be carried out. Namely, in order to obtain the copolymer of the present invention, two or more types of components (C) can be used and this is preferred. As examples of unsaturated monomers having no long-chain alkyl groups with 14 to 22 carbon atoms, mention may be made of, for example, (lower alkyl)acrylates or methacrylates such as methyl acrylate, methyl methacrylate, ethyl acrylate, ethyl methacrylate, n-propyl acrylate, n-propyl methacrylate, isopropyl acrylate, isopropyl methacrylate and the like; (higher alkyl)acrylates or methacrylates having at most 13 carbon atoms such as glycidyl acrylate, glycidyl methacrylate, n-butyl acrylate, n-butyl methacrylate, isobutyl acrylate, isobutyl methacrylate, tert-butyl acrylate, tert-butyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, lauryl methacrylate and the like; lower fatty acid vinyl esters such as vinyl acetate, vinyl propionate and the like; higher fatty acid esters with at most 13 carbon atoms such as vinyl butyrate, vinyl caproate, vinyl 2-ethylhexanoate, vinyl laurate and the like; aromatic vinyl-type monomers such as styrene, vinyltoluene, benzyl acrylate, benzyl methacrylate, phenoxyethyl acrylate, phenoxyethyl methacrylate, vinylpyrrolidone and the like; amino group-containing vinyl-based monomers such as dimethylaminoethyl acrylate, dimethylaminoethyl methacrylate, diethylaminoethyl acrylate, diethylaminoethyl methacrylate and the like; amide group-containing vinyl-type monomers such as acrylamide, methacrylamide, N-methylolacrylamide, N-methylolmethacrylamide, N-methoxymethylacrylamide, N-methoxymethylmethacrylamide, isobutoxymethoxyacrylamide, isobutoxymethoxymethacrylamide, N,N-dimethylacrylamide, N,N-dimethylmethacrylamide and the like; hydroxyl group-containing vinyl-type monomers such as hydroxyethyl acrylate, hydroxyethyl methacrylate, hydroxypropyl alcohol acrylate, hydroxypropyl alcohol methacrylate and the like; carboxylic acid-containing vinyl-type monomers such as acrylic acid, methacrylic acid, itaconic acid, crotonic acid, fumaric acid, maleic acid and the like; ether bond-containing vinyl-type monomers such as tetrahydrofurfuryl acrylate, tetrahydrofurfuryl methacrylate, butoxyethyl acrylate, butoxyethyl methacrylate, ethoxy diethylene glycol acrylate, ethoxy diethylene glycol methacrylate, polyethylene glycol acrylate, polyethylene glycol methacrylate, polypropylene glycol monoacrylate, polypropylene glycol monomethacrylate, hydroxybutyl vinyl ether, cetyl vinyl ether, 2-ethylhexyl vinyl ether and the like; unsaturated group-containing silicone compounds such as acryloxypropyltrimethoxysilane, methacryloxypropyltrimethoxysilane, polydimethylsiloxane containing an acryl group or a methacryl group at one terminal, polydimethylsiloxane having an alkenylaryl group at one terminal and the like; butadiene; vinyl chloride; vinylidene chloride; acrylonitrile, methacrylonitrile; dibutyl fumalate; maleic anhydride; dodecylsuccinic anhydride; acryl glycidyl ether, methacryl glycidyl ether, 3,4-epoxycylcohexylmethyl acrylate, 3,4-epoxycyclohexylmethyl methacrylate; alkali metal salts, ammonium salts, and organic amine salts of radically-polymerizable unsaturated carboxylic acids such as acrylic acid, methacrylic acid, itaconic acid, crotonic acid, fumaric acid, maleinic acid and the like; radically-polymerizable unsaturated monomers having a sulfonic acid group such as styrene sulfonic acid and the like and alkali metal salts, ammonium salts organic amine salts thereof; quaternary ammonium salts derived from acrylic acids or methacrylic acids such as 2-hydroxy-3-methacryloxypropyl trimethylammonium chloride and the like; methacrylic esters of alcohols having tertiary amine groups such as methacrylic acid diethylamine ester and quaternary ammonium salts thereof.

In addition, a polyfunctional vinyl-based monomer can also be used. As examples thereof, mention may be made of, for example, unsaturated group-containing silicone compounds such as trimethylolpropane triacrylate, trimethylolpropane trimethacrylate, pentaerythritol triacrylate, pentaerythritol trimethacrylate, ethylene glycol diacrylate, ethylene glycol dimethacrylate, tetraethylene glycol diacrylate, tetraethylene glycol dimethacrylate, polyethylene glycol diacrylate, polyethylene glycol dimethacrylate, 1,4-butanediol diacrylate, 1,4-butanediol dimethacrylate, 1,6-hexanediol diacrylate, 1,6-hexanediol dimethacrylate, neopentylglycol diacrylate, neopentylglycol dimethacrylate, trimethylolpropane trioxyethylacrylate, trimethylolpropane trioxyethylmethacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, polydimethylsiloxane having both molecular-chain terminals capped with alkenylaryl groups and the like.

In addition, a vinyl-based monomer containing a fluorinated organic group having no long-chain alkyl group with 14 to 22 carbon atoms may be used. The aforementioned vinyl-based monomer containing a fluorinated organic group is preferably one represented by the following general formula: $CH_2=CR^{15}COOR^f$. In the aforementioned formula, $R^{15}$ is a hydrogen atom or a methyl group and $R^f$ is a fluorinated organic group, and as examples thereof, mention may be made of a fluoroalkyl group or a fluoroalkyloxyfluoroalkylene group as described above. As examples of the aforementioned components (A), the compounds represented by the following formulae may be mentioned. In the following formulae, z is an integer ranging from 1 to 4.

$CH_2=CCH_3COO-CF_3$, $CH_2=CCH_3COO-C_2F_5$, $CH_2=CCH_3COO-nC_3F_7$, $CH_2=CCH_3COO-CF(CF_3)_2$, $CH_2=CCH_3COO-nC_4F_9$, $CH_2=CCH_3COO-CF_2CF(CF_3)_2$, $CH_2=CCH_3COO-nC_5F_{11}$, $CH_2=CCH_3COO-nC_6F_{13}$, $CH_2=CCH_3COO-nC_8F_{17}$, $CH_2=CCH_3COO-CH_2CF_3$, $CH_2=CCH_3COO-CH(CF_3)_2$, $CH_2=CCH_3COO-CH_2CH(CF_3)_2$, $CH_2=CCH_3COO-CH_2(CF_2)_2F$, $CH_2=CCH_3COO-CH_2(CF_2)_3F$, $CH_2=CCH_3COO-CH_2(CF_2)_4F$, $CH_2=CCH_3COO-CH_2(CF_2)_6F$, $CH_2=CCH_3COO-CH_2(CF_2)_8F$, $CH_2=CCH_3COO-CH_2CH_2CF_3$, $CH_2=CCH_3COO-CH_2CH_2(CF_2)_2F$, $CH_2=CCH_3COO-CH_2CH_2(CF_2)_3F$, $CH_2=CCH_3COO-CH_2CH_2(CF_2)_4F$, $CH_2=CCH_3COO-CH_2CH_2(CF_2)_6F$, $CH_2=CCH_3COO-CH_2CH_2(CF_2)_8F$, $CH_2=CCH_3COO-CH_2CH_2(CF_2)_{10}F$, $CH_2=CCH_3COO—CH_2CH_2(CF_2)_{12}F$,
$CH_2=CCH_3COO—CH_2CH_2(CF_2)_{14}F$,
$CH_2=CCH_3COO—CH_2CH_2(CF_2)_{16}F$,
$CH_2=CCH_3COO—CH_2CH_2CH_2CF_3$,
$CH_2=CCH_3COO—CH_2CH_2CH_2(CF_2)_2F$,
$CH_2=CCH_3COO—CH_2CH_2CH_2(CF_2)_2H$,
$CH_2=CCH_3COO—CH_2(CF_2)_4H$, $CH_2=CCH_3COO—CH_2CH_2(CF_2)_3H$, $CH_2=CCH_3COO—CH_2CH_2CF(CF_3)—[OCF_2CF(CF_3)]_z—OC_3F_7$, $CH_2=CCH_3COO—CH_2CH_2CF_2CF_2—[OCF_2CF(CF_3)]_z—OC_3F_7$, $CH_2=CHCOO—CF_3$, $CH_2=CHCOO—C_2F_5$, $CH_2=CHCOO-nC_3F_7$, $CH_2=CHCOO—CF(CF_3)_2$, $CH_2=CHCOO-nC_4F_9$, $CH_2=CHCOO—CF_2CF(CF_3)_2$, $CH_2=CHCOO\ -nC_5F_{11}$, $CH_2=CHCOO-nC_6F_{13}$, $CH_2=CHCOO-nC_8F_{17}$, $CH_2=CHCOO—CH_2CF_3$, $CH_2=CHCOO—CH(CF_3)_2$, $CH_2=CHCOO—CH_2CH(CF_3)_2$, $CH_2=CHCOO—CH_2(CF_2)_2F$, $CH_2=CHCOO—CH_2(CF_2)_2F$, $CH_2=CHCOO—CH_2(CF_2)_4F$, $CH_2=CHCOO—CH_2(CF_2)_6F$, $CH_2=CHCOO—CH_2(CF_2)_8F$, $CH_2=CHCOO—CH_2CH_2CF_3$, $CH_2=CHCOO—CH_2CH_2(CF_2)_2F$, $CH_2=CHCOO—CH_2CH_2(CF_2)_3F$, $CH_2=CHCOO—CH_2CH_2(CF_2)_4F$, $CH_2=CHCOO—CH_2CH_2(CF_2)_6F$, $CH_2=CHCOO—CH_2CH_2(CF_2)_8F$, $CH_2=CHCOO—CH_2CH_2(CF_2)_{10}F$, $CH_2=CHCOO—CH_2CH_2(CF_2)_{12}F$, $CH_2=CHCOO—CH_2CH_2(CF_2)_{14}F$, $CH_2=CHCOO—CH_2CH_2(CF_2)_{16}F$, $CH_2=CHCOO—CH_2CH_2CH_2CF_3$, $CH_2=CHCOO—CH_2CH_2CH_2(CF_2)_2F$, $CH_2=CHCOO—CH_2CH_2CH_2(CF_2)_2H$, $CH_2=CHCOO—CH_2(CF_2)_4H$, $CH_2=CHCOO—CH_2CH_2(CF_2)_3H$, $CH_2=CHCOO—CH_2CH_2CF(CF_3)—[OCF_2CF(CF_3)]_z—OC_3F_7$, and $CH_2=CHCOO—CH_2CH_2CF_2CF_2—[OCF_2CF(CF_3)]_z—OC_3F_7$. Among these, the vinyl monomers represented by the following formulae are preferred. $CH_2=CHCOO—CH_2CH_2(CF_2)_6F$, $CH_2=CHCOO—CH_2CH_2(CF_2)_8F$, $CH_2=CCH_3COO—CH_2CH_2(CF_2)_6F$, $CH_2=CCH_3COO—CH_2CH_2(CF_2)_8F$, $CH_2=CHCOO—CH_2CF_3$, and $CH_2=CCH_3COO—CH_2CF_3$.

In particular, the vinyl monomers represented by the following formulae are more preferred. $CH_2=CHCOO—CH_2CF_3$ and $CH_2=CCH_3COO—CH_2CF_3$.

"(Weight of component (C))/(weight of all the monomers constituting the copolymer)" preferably ranges from 0.05 to 0.65, and more preferably ranges from 0.1 to 0.60. If the usage amount of component (C) exceeds the aforementioned upper limit, the grafting amount of the silylalkyl group having the carbosiloxane dendrimer structure and the long-chain alkyl group which are characteristic in the copolymer of the present invention on the main chain of the copolymer may be insufficient, and desirable properties may not be realized in some cases.

In particular, the copolymer of the present invention is preferably obtained by copolymerizing the aforementioned unsaturated monomer having the carbosiloxane dendrimer structure (A), the unsaturated monomer having a long-chain alkyl group with 14 to 22 carbon atoms (B) and at least one unsaturated monomer having no long-chain alkyl groups with 14 to 22 carbon atoms in the weight ratio satisfying the conditions of {(weight of component (A))/(weight of all the monomers)}:{(weight of component (B))/(weight of all the monomers)}:{(weight of component (C))/(weight of all the monomers)} in the range of (0.3 to 0.9):(0.05 to 0.4):(0.05 to 0.65), and {(weight of component (A))/(weight of all the monomers)}≥{(weight of component (B))/(weight of all the monomers)}. In particular, the copolymer in the weight ratio satisfying the conditions of {(weight of component (A))/(weight of all the monomers)}:{(weight of component (B))/(weight of all the monomers)}:{(weight of component (C))/(weight of all the monomers)} in the range of (0.35 to 0.65):(0.05 to 0.4):(0.10 to 0.60), and {(weight of component (A))/(weight of all the monomers)}≥{(weight of component (B))/(weight of all the monomers)} is in particular, preferred. In the copolymer obtained in the aforementioned weight ratio, the silylalkyl group having the carbosiloxane dendrimer structure and the long-chain alkyl group are grafted on the main chain in the specified ratio. For this reason, the aforementioned copolymer is, in particular, preferably used as the copolymer of the present invention.

As the copolymerization method, a radical polymerization method or an ion polymerization method may be used. In particular, a radical polymerization method is preferred, and a solution polymerization method is, in particular, preferably used. The aforementioned solution polymerization method is carried out by reacting the aforementioned unsaturated monomers in a solvent in the presence of a radical initiator for 3 to 20 hours under the temperature condition ranging from 50 to 150° C. As examples of the solvents used herein, mention may be made of aliphatic hydrocarbons such as hexane, octane, decane, cyclohexane and the like; aromatic hydrocarbons such as benzene, toluene, xylene and the like; ethers such as diethyl ether, dibutyl ether, tetrahydrofuran, dioxane and the like; ketones such as acetone, methyl ethyl ketone, methyl isobutyl ketone, diisobutyl ketone and the like; esters such as methyl acetate, ethyl acetate, butyl acetate, isobutyl acetate and the like; alcohols such as methanol, ethanol, isopropyl alcohol, butanol and the like; organosiloxane oligomers such as octamethylcyclotetrasiloxane, decamethylcyclopentasiloxane, hexamethyldisiloxane, octamethyltrisiloxane and the like. As the radical initiator, conventionally known compounds generally used in radical polymerization methods can be employed. As examples thereof, mention may be made of azobis-based compounds such as 2,2'-azobis(isobutyronitrile), 2,2'-azobis(2-methylbutyronitrile), 2,2'-azobis(2,4-dimethylvaleronitrile), dimethyl-2,2'-azobis(2-methyl propionate) and the like; and organic peroxides such as benzoyl peroxide, lauroyl peroxide, tert-butyl peroxybenzoate, tert-butyl peroxy-2-ethylhexanoate and the like. The aforementioned radical initiators may be used alone or in combination of two or more types thereof. The usage amount of the radical initiator preferably ranges from 0.1 to 5 parts by weight with respect to 100 parts by weight of the total of the aforementioned component (A) to component (C). In addition, at the time of polymerization, a chain transfer agent can be added. As examples of the chain transfer agent, mention may be made of mercapto compounds such as 2-mercaptoethanol, butylmercaptan, n-dodecylmercaptan, 3-mercaptopropyltrimethoxysilane, polydimethylsiloxane having a mercaptopropyl group and the like; and halogenated products such as methylene chloride, chloroform, carbon tetrachloride, butyl bromide, 3-chloropropyltrimethoxysilane and the like.

After the polymerization, purification can be carried out by means of a method in which the remaining unreacted vinyl-based monomers are removed by heating under reduced pressure or a method in which a deodorant treatment due to a hydrogenation reaction without a solvent or with a solvent is carried out and light components are removed by distillation by contacting with a nitrogen gas under reduced pressure. In particular, in the case of using as an agent for external use in which reduction of odors and miscibility with other cosmetic components are needed, a purified product obtained as described above is preferably used. In the aforementioned hydrogenation reaction and stripping step, solvents, reaction conditions, reducing pressure conditions and the like used in purification of publicly known organopolysiloxane copolymers can be used without any restrictions and can be freely selected.

In order to further improve adhesive properties of the vinyl-based polymer with respect to skin or hair, or provide appropriate cleansing properties after use, an amino group may be introduced into the side chain of the aforementioned vinyl-based polymer by using an amino group-containing vinyl-based monomer such as dimethylaminoethyl acrylate, dimethylaminoethyl methacrylate, diethylaminoethyl acrylate, diethylaminoethyl methacrylate or the like at a part of the aforementioned component (C), followed by modifying this with an alkali metal salt, an ammonium salt or an amine salt of a halogenated fatty acid such as a potassium salt of monochloroacetic acid, an ammonium salt of monochloroacetic acid, an aminomethylpropanol salt of monochloroacetic acid, a triethanolamine salt of monobromoacetic acid, a sodium salt of monochloropropionic acid or the like. Alternatively, a carboxylic acid group may be introduced into the side chain of the aforementioned vinyl-based polymer by using a carboxylic acid-containing vinyl-based monomer such as acrylic acid, methacrylic acid, itaconic acid, crotonic acid, fumaric acid, maleic acid or the like at a part of the aforementioned component (C), followed by neutralizing this with an amine such as triethylamine, diethylamine, triethanolamine or the like.

The number average molecular weight of the copolymer of the present invention preferably ranges from 3,000 to 2,000,000 and more preferably ranges from 5,000 to 800,000 in view of ease of blending in the cosmetics. As examples of the forms thereof, mention may be made of a liquid, a gum, a paste, a solid and a powder. At the time of blending in the cosmetics, the form of a solution or dispersion in which the copolymer is diluted with a solvent or a powder is preferred. In particular, the copolymer is preferably blended in the cosmetic in the form of a copolymer composition in which the copolymer of the present invention is diluted with an oil agent.

The copolymer of the present invention possesses a film-forming property, and is preferable as a raw material of a cosmetic. Therefore, the copolymer of the present invention can be preferably blended in the cosmetic.

The blending amount of the aforementioned copolymer in the cosmetic of the present invention is not particularly restricted. The cosmetic of the present invention can contain the aforementioned copolymer in an amount ranging from 1 to 99% by weight on the basis of the total weight of the cosmetic. More particularly, the blending amount of the aforementioned copolymer can suitably vary in the range of, for example, 10 to 90% by weight, 20 to 80% by weight, or 30 to 70% by weight, in accordance with the type of the cosmetic.

The cosmetic of the present invention can further comprise an oil agent or agents. As examples of the oil agents, mention may be made of animal oils, vegetable oils, synthetic oils and the like, which are generally used in cosmetics. The aforementioned oil agents may be derived from any origins, may be in the form of a solid, a semi-solid, or a liquid, and may be non-volatile, semi-volatile or volatile, as long as they are hydrophobic. The oil agents are used in order to provide lubricity to skin or hair, make skin flexible, and provide a moisturizing sensation. In addition, the oil agents can also be used in order to obtain a copolymer composition, by diluting the copolymer of the present invention. In particular, as examples thereof, mention may be preferably made of at least one type selected from silicone oils, hydrocarbon oils and fatty acid ester oils which are liquid at 5 to 100° C. The aforementioned oil agents may be blended in the cosmetic of the present invention simultaneously with the aforementioned copolymer composition.

The copolymer of the present invention particularly exhibits superior miscibility with the aforementioned oil agents, and a uniform copolymer composition can be obtained over a long time. The aforementioned composition can be blended in the cosmetic as it is. In view of handling properties, and storage stability thereof, the composition is extremely useful as a raw material of the cosmetic. More particularly, a copolymer composition formed from 100 parts by weight of the copolymer of the present invention and 5 to 1000 parts by weight, preferably 50 to 500 parts by weight and more preferably 100 to 400 parts by weight of the oil agent can be preferably used. In the case of obtaining the copolymer composition by diluting the copolymer of the present invention with the oil agent, a copolymer in which the solvent and unreacted monomers are removed after the polymerization reaction may be uniformly dispersed in the oil agent by means of a mechanical force. Alternatively, the volatile solvent used in the polymerization reaction may be replaced with the aforementioned oil agent.

As the aforementioned oil agents, silicone oils are preferred. The silicone oils are hydrophobic as long as they are oil agents, and the molecular structure thereof may be a cyclic, linear or branched structure. The viscosity of the silicone oils at 25° C. usually ranges from 0.65 to 100,000 mm²/s and preferably ranges from 0.65 to 10,000 mm²/s.

As examples of the aforementioned silicone oils, mention may be made of cyclic organopolysiloxanes, linear organopolysiloxanes, and branched organopolysiloxanes. Among these, volatile linear organopolysiloxanes, branched organopolysiloxanes, and cyclic organopolysiloxanes are preferred.

As the aforementioned silicone oils, for example, organopolysiloxanes represented by the following general formula (3), (4) or (5):

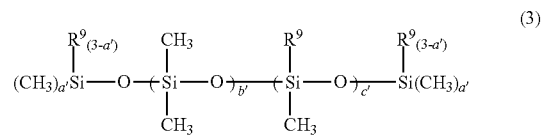

wherein
$R^9$ is a hydrogen atom, a hydroxyl group or a group selected from monovalent non-substituted or fluorine- or amino-substituted $C_{1-30}$ alkyl groups, aryl groups, alkoxy groups and groups represented by $(CH_3)_3SiO\{(CH_3)_2SiO\}_l Si(CH_3)_2CH_2CH_2—$,
wherein l is an integer ranging from 0 to 1,000;
a' is an integer ranging from 0 to 3;
b' is an integer ranging from 0 to 1,000; and
c' is an integer ranging from 0 to 1,000, with the proviso that $1 \le b'+c' \le 2,000$,

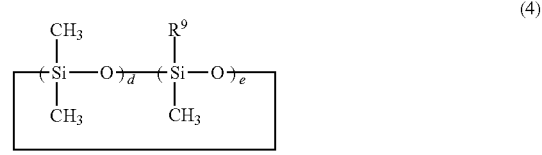

wherein
$R^9$ is the same as defined above;
d is an integer ranging from 0 to 8; and e is an integer ranging from 0 to 8, with the proviso that 3≤d+e≤8,

wherein
R⁹ is the same as defined above;
f is an integer ranging from 1 to 4; and
g is an integer ranging from 0 to 500, can be used.

As examples of monovalent, non-substituted or fluorine- or amino-substituted alkyl groups, aryl groups, and alkoxy groups, having 1 to 30 carbon atoms, mention may be made of, for example, linear or branched alkyl groups having 1 to 30 carbon atoms such as a methyl group, an ethyl group, a propyl group, a butyl group, a pentyl group, a hexyl group, a heptyl group, an octyl group, a decyl group, a dodecyl group and the like; cycloalkyl groups having 3 to 30 carbon atoms such as a cylopentyl group, a cyclohexyl group and the like; aryl groups having 6 to 30 carbon atoms such as a phenyl group, a tolyl group, a xylyl group, a naphthyl group and the like; alkoxy groups having 1 to 30 carbon atoms such as a methoxy group, an ethoxy group, a propoxy group and the like; and substituted groups thereof, in which hydrogen atoms bonded to carbon atoms of the aforementioned groups are at least partially substituted by a fluorine atom or an amino group. A non-substituted alkyl group or aryl group is preferred, and a non-substituted alkyl group having 1 to 6 carbon atoms or aryl group is further preferred. A methyl group, an ethyl group or a phenyl group is, in particular, preferred.

More particularly, as examples of the silicone oils having the aforementioned structures, the following organopolysiloxanes may be mentioned. As examples of cyclic organopolysiloxanes, mention may be made of hexamethylcyclotrisiloxane (D3), octamethylcyclotetrasiloxane (D4), decamethylcyclopentasiloxane (D5), dodecamethylcyclohexasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl)trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, tetra(N,N-bis(lauroyl)-3-aminopropyl)tetramethylcyclotetrasiloxane and the like.

As examples of linear organopolysiloxanes, mention may be made of a dimethylpolysiloxane in which both molecular terminals are capped with trimethylsiloxy groups (dimethylsilicone with a low viscosity such as 2 cst or 6 cst to dimethylsilicone with a high viscosity such as 1,000,000 cst), an organohydrogenpolysiloxane, a methylphenylpolysiloxane in which both molecular terminals are capped with trimethylsiloxy groups, a copolymer of methylphenylsiloxane and dimethylsiloxane in which both molecular terminals are capped with trimethylsiloxy groups, a diphenylpolysiloxane in which both molecular terminals are capped with trimethylsiloxy groups, a copolymer of diphenylsiloxane and dimethylsiloxane in which both molecular terminals are capped with trimethylsiloxy groups, a trimethylpentaphenyltrisiloxane, a phenyl(trimethylsiloxy)siloxane, a methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl(3,3,3-trifluoropropyl)siloxane and dimethylsiloxane in which both molecular terminals are capped with trimethylsiloxy groups, an α,ω-dihydroxypolydimethylsiloxane, an α,ω-diethoxypolydimethylsiloxane, a 1,1,1,3,5,5,5-heptamethyl-3-octyltrisiloxane, a 1,1,1,3,5,5,5-heptamethyl-3-dodecyltrisiloxane, a 1,1,1,3,5,5,5-heptamethyl-3-hexadecyltrisiloxane, a tristrimethylsiloxymethylsilane, a tristrimethylsiloxyalkylsilane, a tetrakistrimethylsiloxysilane, tetramethyl-1,3-dihydroxydisiloxane, an octamethyl-1,7-dihydroxytetrasiloxane, a hexamethyl-1,5-diethoxytrisiloxane, a hexamethyldisiloxane, an octamethyltrisiloxane, a higher alkoxy-modified silicone, a higher fatty acid-modified silicone and the like.

As examples of branched organopolysiloxanes, mention may be made of methyltristrimethylsiloxysilane, ethyltristrimethylsiloxysilane, propyltristrimethylsiloxysilane, tetrakistrimethylsiloxysilane, phenyltristrimethylsiloxysilane and the like.

When at least one of the aforementioned silicone oils is contained in the cosmetic of the present invention, stability of the cosmetic over time can be improved, and a refreshing feeling to the touch which the silicone oils inherently possess can be realized.

The oil agents other than the silicone oils are preferably in the form of a liquid at 5 to 100° C. As the oil agents other than the silicone oils, hydrocarbon oils and/or fatty acid ester oils are preferred. They may be used alone, but preferably used in combination with the aforementioned silicone oils. By using the aforementioned silicone oils in combination with the hydrocarbon oils and/or fatty acid ester oils, advantages can be obtained in that moisture on the skin can be maintained, and a moisturizing sensation (also referred to as "moisturizing feeling to the touch") such as moisturizing skin or hair and smooth feeling to the touch, in addition to the refreshing feeling to the touch which the silicone oils inherently possess, can be provided in cosmetics, and stability over time of cosmetics is not impaired. In addition, use of the cosmetics containing the aforementioned silicone oils in combination with the hydrocarbon oils and/or fatty acid ester oils provides advantages in that the aforementioned moisturizing components can be stably and uniformly applied on the skin or hair, the moisturizing effects of the moisturizing components on the skin are increased, and superior smoothness and moisturizing feeling can be provided as compared with cosmetics containing only oil agents other than silicone oils (the hydrocarbon oils and/or fatty acid ester oils).

As examples of hydrocarbon oils, mention may be made of liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene and the like.

As examples of fatty acid ester oils, mention may be made of hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl, dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-hexanoate, trimethylolpropane tri-2-ethylhexanoate, ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, dipentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethyleneglycol distearate), diisopropyl dimmer dilinoleate, diisostearyl dimmer dilinoleate, di(isostearyl/phytosteryl) dimmer dilinoleate, (phytosteryl/behenyl) dimmer dilinoleate, (phytosteryl/isostearyl/cetyl/stearyl/behenyl) dimmer dilinoleate, dimmer dilinoleyl dimmer dilinoleate, dimmer dilinoleyl diisostearate, dimmer dilinoleyl hydrogenated rosin condensate, dimmer dilinoleic acid hardened castor oil, hydroxyalkyl dimmer dilinoleyl ether, glyceryl triisooctanoate, glyceryl triisostearate, glyceryl trimyristate; glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester, gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of *macadamia* nut oil fatty acid, phytosteryl ester of *macadamia* nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like.

In addition thereto, fats and oils, higher alcohols, higher fatty acids, fluorine-based oils and the like may be used in combination of two or more types thereof. For example, the oil agents described below may also be used in combination of two or more types. Hereinafter, the oil agents other than silicone oils, hydrocarbon oils and fatty acid ester oils, which can be used in the present invention, are described in detail.

As examples of natural animal or vegetable fats and oils and semi-synthetic fats and oils, mention may be made of avocado oil, linseed oil, almond oil, ibota wax, *perilla* oil, olive oil, cacao butter, kapok wax, kaya oil, carnauba wax, liver oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, *macadamia* nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil and the like, with the proviso that POE means polyoxyethylene.

As examples of higher alcohols, mention may be made of lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glyceryl ether (selachyl alcohol) and the like.

As examples of higher fatty acids, mention may be made of, for example, lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

As examples of fluorine-based oils, mention may be made of perfluoro polyether, perfluorodecalin, perfluorooctane and the like.

In the cosmetics of the present invention, one or more surfactants selected from the group consisting of anionic surfactants, cationic surfactants, nonionic surfactants, amphoteric surfactants and semi-polar surfactants can be used together.

Hereinafter, they are described in detail.

As examples of anionic surfactants, mention may be made of saturated or unsaturated fatty acid salts such as sodium laurate, sodium stearate, sodium oleate, sodium linoleate and the like; alkylsulfuric acid salts; alkylbenzenesulfonic acids such as hexylbenzenesulfonic acid, octylbenzenesulfonic acid, dodecylbenzenesulfonic acid and the like, as well as salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamidesulfuric acid salts; alkyl- or alkenylphosphoric acid salts; alkylamidephosphoric acid salts; alkyloylalkyl taurine salts; N-acylamino acid salts; sufosuccinic acid salts; alkyl ether carboxylic acid salts; amide ether carboxylic acid salts; α-sulfofatty acid ester salts; alanine derivatives; glycine derivatives; and arginine derivatives. As examples of salts, mention may be made of alkali metal salts such as a sodium salt and the like, alkaline earth metal salts such as a magnesium salt and the like, alkanolamine salts such as a triethanolamine salt and the like, and ammonium salts.

As examples of cationic surfactants, mention may be made of alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE) oleylmethylammonium (2EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, stearic acid diethylaminoethylamide, stearic acid dimethylaminopropylamide, behenic acid amide propyldimethylhydroxypropylammonium chloride, stearoyl colaminoformyl methylpyridinium chloride, cetylpyridinium chloride, tall oil alkylbenzyl hydroxyethylimidazolinium chloride, and benzylammonium salt.

As examples of nonionic surfactants, mention may be made of polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hardened) castor oils, polyoxyalkylene alkyl phenols, polyoxyalkylene alkyl phenyl ethers, polyoxyalkylene phenyl, phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethylene glycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers.

As examples of amphoteric surfactants, mention may be made of imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. More particularly, as examples thereof, mention may be made of imidazoline-type amphoteric surfactants such as sodium 2-undecyl-N, N, N-(hydroxyethylcarboxymethyl)-2-imidazoline, 2-cocoyl-2-imidazolinium hydroxide-1-carboxyethyloxy disodium salt and the like; alkylbetaine-type amphoteric surfactants such as lauryl dimethylaminoacetic acid betaine, myristyl betaine and the like; and amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric amidopropyl dimethylamino acetic acid betaine, myristic amidopropyldimethylamino acetic acid betaine, palmitic amidopropyldimethylamino acetic acid betaine, stearic amidopropyl dimethylamino acetic acid betaine, oleic amidopropyl dimethylamino acetic acid betaine and the like; alkyl sulfobetaine-type amphoteric surfactants such as coconut oil fatty acid dimethyl sulfopropyl betaine and the like; alkylhydroxy Sulfobetaine-type amphoteric surfactants such as lauryl dimethylaminohydroxy sulfobetaine and the like; phosphobetaine-type amphoteric surfactants such as laurylhydroxy phosphobetaine and the like; amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine and the like.

As examples of semi-polar surfactants, mention may be made of alkylamine oxide-type surfactants, alkylamine oxides, alkylamide amine oxides, alkylhydroxyamine oxides and the like. Alkyldimethylamine oxides having 10 to 18 carbon atoms, alkoxyethyl dihydroxyethylamine oxides having 8 to 18 carbon atoms and the like are preferably used. More particularly, as examples thereof, mention may be made of dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide, ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

The cosmetics of the present invention can contain various cosmetic raw material(s), in addition to the aforementioned components. The aforementioned raw materials are preferably hydrophobic so that they are not dissolved in water at all or have a solubility below 1% by weight with respect to 100 g of water. As examples of the aforementioned cosmetic raw materials, mention may be made of, for example, powders, coloring agents, water-soluble polymers, oil-soluble gelling agents, organo-modified clay minerals, silicone gums, silicone resins, silicone elastomers, organo-modified silicones, UV-ray protective components and the like.

With respect to powders and/or coloring agents, there is no restriction on the form thereof (sphere, bar, needle, plate, amorphous, spindle or the like), the particle size (aerosol, microparticle, pigment-grade, or the like), and the particle structure (porous, non-porous or the like) thereof, and any one thereof can be used, as long as the powders are commonly used in cosmetics. In the case of blending the aforementioned powders and/or coloring agents in cosmetics as pigments, one type or two or more types of powders selected from inorganic powders, organic powders, and resin powders, having an average particle size ranging from 1 nm to 20 μm, are preferably blended.

As examples of powders and/or coloring agents, mention may be made of, for example, inorganic powders, organic powders, surfactant metal salt powders (metallic soaps), colored pigments, pearl pigments, metal powder pigments and the like. In addition, hybrid products of the aforementioned pigments can also be used.

More particularly, as examples of inorganic powders, mention may be made of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, and the like. As examples of organic powders, mention may be made of polyamide powder, polyester powder, polyethylene powder, polypropylene powder, polystyrene powder, polyurethane powder, benzoguanamine powder, polymethylbenzoguanamine powder, polytetrafluoroethylene powder, poly(methyl methacrylate) powder, cellulose, silk powder, nylon powder, nylon 12, nylon 6, silicone powder, silicone gum powder, silicone elastomer spherical powder the surface of which is coated with polymethylsilsesquioxane, polymethylsilsesquioxane spherical powder, copolymers of styrene and acrylic acid, copolymers of divinylbenzene and styrene, vinyl resin, urea resin, phenol resin, fluorine resin, silicon resin, acrylic resin, melamine resin, epoxy resin, polycarbonate resin, microcrystalline fiber powder, starch powder, lauroyl lysine and the like.

As examples of surfactant metal salt powders, mention may be made of zinc, stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like.

As examples of colored pigments, mention may be made of inorganic red pigments such as red iron oxide, iron oxide, iron hydroxide, iron titanate and the like; inorganic brown pigments such as gamma-iron oxide and the like; inorganic yellow pigments such as yellow iron oxide, ocher, and the like; inorganic black iron pigments such as black iron oxide, carbon black and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red, No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow. No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207 and the like; and laked pigments of natural pigments such as carminic acid, laccaic acid, carthamin, brazilin, crocin and the like.

As examples of pearl pigments, mention may be made of titanium oxide-coated mica, titanium mica; iron oxide-coated titanium mica, titanium oxide-coated mica, bismuth oxychloride, titanium oxide-coated bismuth oxychloride, titanium oxide-coated talc, fish scale foil, titanium oxide-coated colored mica, and the like. As examples of metal powder pigments, mention may be made of powders of metals such as aluminum, gold, silver, copper, platinum, stainless steel, and the like.

In addition, in the aforementioned powders and/or coloring agents, a part or all parts thereof may be, in particular, preferably subjected to a water-repellent treatment. In addition, composite products in which the aforementioned powders and/or coloring agents are mutually composited or surface-treated products in which the aforementioned powders and/or coloring agents are subjected to a surface treatment with a general oil agent, a silicone compound other than the organopolysiloxane copolymer of the present invention, a fluorine compound, a surfactant or the like can also be used. One type thereof or two or more types thereof can be used, if necessary. The blending amount of the aforementioned powders and/or coloring agents preferably ranges from 0.1 to 99% by weight with respect to the total amount of the cosmetic. In particular, in the case of a powdery solid cosmetic, the blending amount of the aforementioned powders and/or coloring agents preferably ranges from 80 to 99% by weight with respect to the total amount of the cosmetic.

As examples of other water-repellant treatments, mention may be made of treatments in which the aforementioned powders and/or coloring agents are treated with various water-repellent surface treatment agents, such as organosiloxane treatments such as a methylhydrogenpolysiloxane treatment, a silicone resin treatment, a silicone gum treatment, an acryl silicone treatment, a fluorinated silicone treatment and the like; metallic soap treatments such as a zinc stearate treatment and the like; silane treatments such as a silane coupling agent treatment, an alkylsilane treatment and the like; fluorine compound treatments such as a perfluoroalkylsilane treatment, a perfluoroalkyl phosphate treatment, a perfluoro polyether treatment and the like; amino acid treatments such as an N-lauroyl-L-lysine treatment and the like; oil agent treatments such as a squalane treatment and the like; acryl treatments such as an alkyl acrylate treatment and the like. The aforementioned treatments can be used in combination of one or more types thereof.

As the water-soluble polymers, one type or two or more types thereof can be used. As examples of natural water-soluble polymers, mention may be made of vegetable-based polymers such as gum Arabic, tragacanth gum, galactan, guar gum, carob gum, Karaya gum, carrageenan, pectin, agar, quince seed, algal colloide, starch (rice, corn, potato, or wheat), glycyrrhizinic acid and the like; microorganism-based polymers such as xanthan gum, dextran, succinoglucan, pullulan, and the like; and animal-based polymers such as collagen, casein, albumin, gelatin, and the like. In addition, as examples of semi-synthetic water-soluble polymers, mention may be made of, for example, starch-based polymers such as carboxymethyl starch, methyhydroxypropyl starch, and the like; cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, cellulose powder, and the like; and alginate-based polymers such as sodium alginate, propylene glycol alginate and the like. As examples of synthetic water-soluble polymers, mention may be made of, for example, vinyl-based polymers such as polyvinyl alcohol, polyvinyl methyl ether-based polymer, polyvinylpyrrolidone, carboxyvinyl polymer (CARBOPOL 940, 941; manufactured by BF Goodrich Corporation) and the like; polyoxyethylene-based polymers such as polyethylene glycol 20,000, polyethylene glycol 6,000, polyethylene glycol 4,000 and the like; copolymer-based polymers such as a copolymer of polyoxyethylene and polyoxypropylene, PEG/PPG methyl ether and the like; acryl-based polymers such as poly(sodium acrylate), poly(ethyl acrylate), polyacrylamide and the like; polyethylene imines; cationic polymers and the like.

As examples of other cationic water-soluble polymers, in particular, as components which are preferably blended in hair cosmetics, mention may be made of quaternary nitrogen-modified polysaccharides such as cation-modified cellulose, cation-modified hydroxyethylcellulose, cation-modified guar gum, cation-modified locust bean gum, cation-modified starch and the like; dimethyldiallylammonium chloride derivatives such as a copolymer of dimethyldiallylammonium chloride and acrylamide, poly(dimethylmethylene piperidinium chloride) and the like; and vinylpyrrolidone derivatives such as a salt of a copolymer of vinylpyrrolidone and dimethylaminoethyl methacrylic acid, a copolymer of vinylpyrrolidone and methacrylamide propyltrimethylammonium chloride, a copolymer of vinylpyrrolidone and methylvinylimidazolium chloride and the like.

As examples of oil-soluble gelling agents, mention may be made of metallic soaps such as aluminum stearate, magnesium stearate, zinc myristate and the like; amino acid derivatives such as N-lauroyl-L-glutamic acid, α,γ-di-n-butylamine and the like; dextrin fatty acid esters such as dextrin palmitate, dextrin stearate, dextrin 2-ethylhexanoate palmitate and the like; sucrose fatty acid esters such as sucrose palmitate, sucrose stearate and the like; benzylidene derivatives of sorbitol such as monobenzylidene sorbitol, dibenzylidene sorbitol and the like; and the like. The oil-soluble gelling agents can be used alone or in combination of two or more types thereof, if necessary.

As examples of organo-modified clay minerals, mention may be made of, for example, dimethylbenzyldodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium silicate and the like. As examples of commercially available products thereof, mention may be made of Benton 27 (benzyldimethylstearylammonium chloride-treated hectorite, manufactured by Nationalred Co.), Benton 38 (distearyldimethylammonium chloride-treated hectorite, manufactured by Nationalred Co.) and the like.

The silicone gum is a linear diorganopolysiloxane having an ultra-high degree of polymerization, and is also referred to as a silicone raw rubber or an organopolysiloxane gum. The silicone raw rubber possesses a high degree of polymerization, and for this reason, it has a measurable degree of plasticity. In view of this, the silicone raw rubber is different from the aforementioned oil silicones. As examples of the aforementioned-silicone raw rubber, mention may be made of substituted or non-substituted organopolysiloxanes having a dialkylsiloxy unit (D unit) such as dimethylpolysiloxane, methylphenylpolysiloxane, aminopolysiloxane, methylfluoroalkylpolysiloxane and the like, or those having a micro-crosslinking structure thereof and the like. As representative examples thereof, there are those represented by the following general formula:

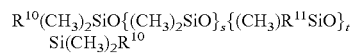

wherein $R^{11}$ is a group selected from a vinyl group, a phenyl group, an alkyl group having 6 to 20 carbon atoms, an aminoalkyl group having 3 to 15 carbon atoms, a perfluoroalkyl group having 3 to 15 carbon atoms, and a quaternary ammonium salt group-containing alkyl group having 3 to 15 carbon atoms; the terminal $R^{10}$ is a group selected from an alkyl group having 1 to 8 carbon atoms, a phenyl group, a vinyl group, an aminoalkyl group having 3 to 15 carbon atoms, a hydroxyl group and an alkoxy group having 1 to 8 carbon atoms; s=2,000 to 6,000; t=0 to 1,000; and s+t=2,000 to 6,000. Among these, a dimethylpolysiloxane raw rubber having a degree of polymerization ranging from 3,000 to 20,000 is preferred.

The silicone resin is an organopolysiloxane with a highly branched molecular structure, a net-like molecular structure or a cage-like molecular structure, and may be in the form of a liquid or solid at room temperature. Any silicone resins usually used in cosmetics can be used unless they are contrary to the purposes of the present invention. As examples of the solid silicone resins, mention may be made of, for example, MQ resins, MDQ resins, MTQ resins, MDTQ resins, TD resins, TQ resins, or TDQ resins comprising any combinations of a triorganosiloxy unit (M unit) (wherein the organo group is a methyl group alone, or a methyl group in combination with a vinyl group or a phenyl group), a diorganosiloxy unit (D unit) (wherein the organo group is a methyl group alone, or a methyl group in combination with vinyl group or phenyl group), a monoorganosiloxy unit (T unit) (wherein the organo group is a methyl group, a vinyl group or a phenyl group), and a siloxy unit (Q unit). In addition, as other examples thereof, mention may be made of trimethylsiloxysilicic acid, polyalkylsiloxysilicic acid, trimethylsiloxysilicic acid containing dimethylsiloxy units and alkyl(perfluoroalkyl) siloxysilicic acid. The aforementioned silicone resins are preferably oil soluble, and, in particular, preferably are soluble in D4 or D5.

A silicone elastomer in any form can be blended in the cosmetic in accordance with the purpose thereof. In particular, the silicone elastomer is preferably blended as organopolysiloxane elastomer spherical powders or a crosslinking organopolysiloxane.

The silicone elastomer powders mainly correspond to a crosslinked product of a linear diorganopolysiloxane, and can be in various forms such as a spherical form, a flat form, an amorphous form and the like. The elastomer may be in the form of an oil dispersant without shapes. In the cosmetic of the present invention, silicone elastomer powders in the form of particles are preferred, which have a primary particle size observed by an electronic microscope and/or an average primary particle size measured by a laser diffraction/scattering method ranging from 0.1 to 50 µm, and in which the primary particle is in the spherical form. In addition, the silicone elastomer constituting the silicone elastomer powder has a hardness preferably not exceeding 80, and more preferably not exceeding 65, when measured by means of a type A durometer according to JIS K 6253 "Method for determining hardness of vulcanized rubber or thermoplastic rubber".

The organopolysiloxane elastomer spherical powders may be optionally subjected to a surface treatment with a silicone resin, a silica or the like. As examples of the aforementioned silicone elastomer powders, mention may be made of, for example, those described in Japanese Unexamined Patent Application, First Publication No. H02-243612; Japanese. Unexamined Patent Application, First Publication No. H08-12545; Japanese Unexamined Patent Application, First Publication No. H08-12546; Japanese Unexamined Patent Application, First Publication No. H08-12524; Japanese Unexamined Patent Application, First Publication No. H09-241511; Japanese Unexamined Patent. Application, First Publication No. H10-36219; Japanese Unexamined Patent Application, First Publication No. H11-193331; Japanese Unexamined Patent Application, First Publication No. 2000-281523 and the like. The crosslinking silicone powders listed in "Japanese Cosmetic Ingredients Codex (JCIC)" correspond thereto. As commercially available products of organopolysiloxane elastomer spherical powders, there are Trefil E-506S, Trefil E-508, 9701 Cosmetic Powder, and 9702 Powder, manufactured by Dow Corning Toray Co., Ltd., and the like. The aforementioned silicone elastomer powders may be subjected to a surface treatment. As examples of the surface treatment agents, mention may be made of methylhydrogenpolysiloxane, silicone resins, metallic soap, silane coupling agents, silica, inorganic oxides such as titanium oxide and the like and fluorine compounds such as perfluoroalkylsilane, perfluoroalkyl phosphoric ester salts and the like.

In addition, the organopolysiloxane elastomer spherical powders in the form of an aqueous dispersion can also be used in the cosmetic of the present invention. As examples of commercially available products of the aforementioned aqueous dispersion, mention may be made of, for example, "BY29-129" and "PF-2001 PIF Emulsion" manufactured by Dow Corning Toray Co., Ltd., and the like. By blending an aqueous dispersion (=suspension) of the aforementioned silicone elastomer powders, the sensation during use of the cosmetics of the present invention can be further improved, and from this point of view, the silicone elastomer powders are extremely useful.

As the crosslinking organopolysiloxanes, non-emulsifiable organopolysiloxanes without hydrophilic parts such as polyoxyalkylene units which have a three-dimensional crosslinked structure by a reaction between the organopolysiloxane chains and the crosslinking components and the like are preferred. The aforementioned crosslinking organopolysiloxanes can be used without restrictions of physical modes and preparation methods such as dilution, properties and the like. As particularly preferable examples thereof, mention may be made of α,ω-diene crosslinking silicone elastomers (as commercially available products, DC 9040 Silicone Elastomer Blend, DC 9041 Silicone Elastomer Blend, DC 9045 Silicone Elastomer. Blend, and DC 9046 Silicone Elastomer Blend, manufactured by Dow Corning Corporation in the USA) described in U.S. Pat. No. 5,654,362.

The organo-modified silicones are preferably lipophilic. As examples thereof, mention may be made of amino-modified silicones, amino polyether-modified silicones, epoxy-modified silicones, carboxyl-modified silicones amino acid-modified silicones, carbinol-modified silicones, acryl-modified silicones, phenol-modified silicones, amidoalkyl-modified silicones, aminoglycol-modified silicones, and alkoxy-modified silicones. The aforementioned organo-modified silicones may have an alkylene chain, an amino-alkylene chain or a polyether chain, in addition to the polysiloxane bonds as a main chain, with a degree such that the compound does not exhibit hydrophilic properties, and the organo-modified group may exist at the side chain or at one terminal or both terminals of the polysiloxane chain. In the case of using the cosmetics of the present invention as hair cosmetics, amino-modified silicones, carbinol-modified silicones, amino polyether-modified silicones, or amino glycol-modified silicones can be preferably used. As general examples thereof, amino-modified silicones having a 3-aminopropyl group, an N-(2-aminoethyl)-3-aminopropyl group and the like can be mentioned.

Among UV-ray protective components, there are inorganic UV-ray protective components and organic UV-ray protective components. If the cosmetics of the present invention are sunscreen cosmetics, at least one type of inorganic or organic UV-ray protective component, and in particular, an organic UV-ray protective component is preferably contained.

The inorganic UV-ray protective components may be components in which the aforementioned inorganic powder pigments, metal powder pigments and the like are blended as UV-ray dispersants. As, examples thereof, mention may be made of metal oxides such as titanium oxide, zinc oxide, cerium oxide, titanium suboxide, iron-doped titanium oxides and the like; metal hydroxides such as iron hydroxides and the like; metal flakes such as platy iron oxide, aluminum flake and the like; and ceramics such as silicon carbide and the like. Among these, at least one type of a material selected from fine particulate metal oxides or fine particulate metal hydroxides with an average particle size ranging from 1 to 100 nm in the form of granules, plates, needles, or fibers is, in particular, preferred. The aforementioned powders are preferably subjected to conventional surface treatments such as fluorine compound treatments, among which a perfluoroalkyl phosphate treatment; a perfluoroalkylsilane treatment, a perfluoropolyether treatment, a fluorosilicone treatment, and a fluorinated silicone resin treatment are preferred; silicone treatments, among which a methylhydrogenpolysiloxane treatment, a dimethylpolysiloxane treatment, and a vapor-phase tetramethyltetrahydrogencyclotetrasiloxane treatment are preferred; silicone resin treatments, among which a trimethylsiloxysilicic acid treatment is preferred; pendant treatments which are methods of adding alkyl chains after the vapor-phase silicone treatment; silane coupling agent treatments; titanium coupling agent treatments; silane treatments among which an alkylsilane treatment and an alkylsilazane treatment are preferred; oil agent treatments; N-acylated lysine treatments; polyacrylic acid treatments; metallic soap treatments in which a stearic acid salt or a myristic acid salt is preferably used; acrylic resin treatments; metal oxide treatments and the like. A plurality of the treatments described above are preferably carried out. For example, the surface of the fine particulate titanium oxide is coated with a metal oxide such as silicon oxide, alumina or the like, and then, a surface treatment with an alkylsilane is carried out. The total amount of the material used for the surface treatment preferably ranges from 0.1 to 50% by weight based on the amount of the powder.

The organic UV-ray protective components are lipophilic UV-ray protective components. As examples thereof, mention may be made of benzoic acid-based UV-ray absorbers such as paraminobenzoic acid (hereinafter, referred to as PABA), PABA monoglycerol ester, N,N-dipropoxy-PABA ethyl ester, N,N-diethoxy-PABA ethyl ester, N,N-dimethyl-PABA ethyl ester, N,N-dimethyl-PABA butyl ester and the like; anthranilic acid-based UV-ray absorbers such as homomethyl N-acetylanthranilate and the like; salicylic acid-based UV-ray absorbers such as amyl salicylate, menthyl salicylate, homomethyl salicylate, octyl salicylate, phenyl salicylate, benzyl salicylate, p-isopropanolphenyl salicylate and the like; cinnamic acid-based UV-ray absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methdxycinnamate (2-ethylhexyl p-methoxycinnamate), 2-ethoxyethyl p-methoxycinnamate, cyclohexyl p-methoxy cinnamate, ethyl α-cyano-β-phenylcinnamate, 2-ethylhexyl α-cyano-β-phenylcinnamate, glyceryl mono-2-ethylhexanoyl-diparamethoxycinnamate, 3-methyl 4-[methylbis(trimethylsiloxy)silyl]butyl 3,4,5-trimethoxycinnamate and the like; benzophenone-based UV-ray absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone 5-sulfonate, 4-phenylbenzophenone, 2-ethylhexyl-4'-phenylbenzophenone 2-carboxylate, hydroxy-4-n-octoxybenzophenone, 4-hydroxy-3-carboxybenzophenone and the like; 3-(4'-methylbenzylidene)-d,l-camphor; 3-benzylidene-d,l-camphor; urocanic acid; ethyl urocanate; 2-phenyl-5-methylbenzoxazole; 2,2'-hydroxy-5-methylphenyl benzotriazole; 2-(2'-hydroxy-5'-t-octylphenyl)benzotriazole; 2-(2'-hydroxy-5'-methylphenyl)benzotriazole; dibenzaladine; dianisoylmethane; 4-methoxy-4'-t-butylbenzoylmethane; 5-(3,3-dimethyl-2-norbonylidene)-3-pentan-2-one and the like.

Furthermore, hydrophobic polymer powders containing the aforementioned organic UV-ray protective components inside thereof can also be used. The polymer powder may be hollow or not, may have an average primary particle size thereof ranging from 0.1 to 50 μm and may have a particle size distribution thereof of either broad or sharp. As examples of the polymers, mention may be made of acrylic resins, methacrylic resins, styrene resins, polyurethane resins, polyethylene, polypropylene, polyethylene terephthalate, silicone resins, nylons, acrylamide resins, and silylated polypeptide resins. Polymer powders containing the organic UV-ray protective components in an amount ranging from 0.1 to 30% by weight with respect to the amount of the powder are preferred. Polymer powders containing 4-tert-butyl-4'-methoxydibenzoylmethane, which is a UV-A absorber, are particularly preferred.

The UV-ray protective components which can be preferably used in the cosmetics of the present invention are at least one type of compound selected from the group consisting of fine particulate titanium oxide, fine particulate zinc oxide, 2-ethylhexyl paramethoxycinnamate, 4-tert-butyl-4'-methoxydibenzoylmethane, and benzophenone-based UV-ray absorbers. The aforementioned UV-ray protective components are commonly used and easily available, and exhibit superior effects of preventing ultraviolet rays. For these reasons, the aforementioned UV-ray protective components are preferably used. In particular, inorganic UV-ray protective components and organic UV-ray protective components are preferably used in combination. In addition, UV-A protective components and UV-B protective components are further preferably used in combination.

In the cosmetics of the present invention, other components usually used in cosmetics can be blended within a range which does not impair the effects of the present invention, such as alcohols, organic resins, humectants, preservatives, anti-microbial agents, perfume, salts, antioxidants, pH adjustors, chelating agents, algefacient agents, anti-inflammatory agents, components for beautifying the skin (such as whitening agents, cell activators, agents for ameliorating skin roughness, blood circulation accelerators, astringents, antiseborrheic agents and the like), vitamins, amino acids, nucleic acids, hormones, clathrate compounds and the like. They are not particularly restricted thereto.

As the alcohols, one type or two or more types of polyhydric alcohols and/or lower monovalent alcohols can be used. As examples of lower alcohols, mention may be made of ethanol, isopropanol, n-propanol, t-butnol, s-butanol and the like. As examples of polyhydric alcohols, mention may be made of divalent alcohols such as 1,3-butylene glycol, 1,2-butylene glycol, propylene glycol, trimethylene glycol, tetramethylene glycol, 2,3-butylene glycol, pentamethylene glycol, 2-butene-1,4-diol, dibutylene glycol, pentyl glycol, hexylene glycol, octylene glycol and the like; trivalent alcohols such as glycerol, trimethylolpropane, 1,2,6-hexanetriol and the like; polyhydric alcohols having tetra- or more valences such as pentaerythritol, xylitol and the like; sugar alcohols such as sorbitol, mannitol, maltitol, maltotriose, sucrose, erytritol, glucose, fructose, starch decomposed products, maltose, xylitose, starch decomposed reduction alcohols and the like. In addition to the aforementioned polyhydric alcohols having a low molecular weight, mention may be made of polyhydric alcohol polymers such as diethylene glycol, dipropylene glycol, triethylene glycol, polypropylene glycol, tetraethylene glycol, diglycerol, polyethylene glycol, triglycerol, tetraglycerol, polyglycerol and the like. Among these, 1,3-butylene glycol, sorbitol, dipropylene glycol, glycerol, and polyethylene glycol are, in particular, preferred. The blending amount thereof preferably ranges from 0.1 to 50% by weight with respect to the total amount of the cosmetic.

As examples of organic resins, mention may be made of polyvinyl alcohol, polyvinylpyrrolidone, poly(alkyl acrylate) copolymer and the like.

As examples of humectants, mention may be made of, for example, hyaluronic acid, chondroitin sulfate, pyrrolidone carboxylic acid salts, polyoxyethylene methylglucoside, polyoxypropylene methylglucoside, and the like. Needless to say, the aforementioned polyhydric alcohols exhibit a function of retaining moisture on the skin or hair.

As examples of the preservatives, mention may be made of, for example, alkyl paraoxybenzoates, benzoic acid, sodium benzoate, sorbic acid, potassium sorbate, phenoxyethanol and the like. As examples of the antimicrobial agents, mention may be made of benzoic acid, salicylic acid, carbolic acid, sorbic acid, alkyl paraoxybenzoates, parachloromethacresol, hexachlorophene, benzalkonium chloride, chlorhexidine chloride, trichlorocarbanilide, trichlosan, photosensitizers and the like. In the case of lipsticks, the aforementioned compounds are not preferably contained.

As examples of perfume, mention may be made of perfume extracted from flowers, seeds, leaves, and roots of various plants; perfume extracted from seaweeds; perfume extracted from various parts or secretion glands of animals such as musk and sperm oil; or artificially synthesized perfume such as menthol, musk, ethyl acetate, and vanilla. The perfume are blended in the cosmetics in order to impart the cosmetics with a certain aroma or scent, or in order to mask unpleasant odor.

As examples of antioxidants, mention may be made of, for example, tocopherol, butylhydroxyanisole, dibutylhydroxytoluene, phytic acid and the like.

As examples of pH adjustors, mention may be made of, for example, lactic acid, citric acid, glycolic acid, succinic acid, tartaric acid, dl-malic acid, potassium carbonate, sodium hydrogencarbonate, ammonium hydrogencarbonate and the like.

As examples of chelating agents, mention may be made of, for example, alanine, sodium salt of edetic acid, sodium polyphosphate, sodium metaphosphate, phosphoric acid and the like.

As examples of algefacient agents, mention may be made of l-menthol, camphor and the like.

As examples of anti-inflammatory agents, mention may be made of ε-aminocaproic acid, glycyrrhizinic acid, β-glycyrrhetinic acid, lysozyme chloride, guaiazulene, hydrocortisone, allantoin, tranexamic acid, azulene and the like.

As examples of skin-beautifying components, mention may be made of whitening agents such as placenta extracts, arbutin, glutathione, saxifrageous extracts and the like; cell activators such as royal jelly, and the like; agents for ameliorating skin roughness; blood circulation accelerators such as nonylic acid vanillylamide, benzyl nicotinate, beta-butoxyethyl nicotinate, capsaicin, gingerone, cantharide tincture, ichthammol, caffeine, tannic acid, alpha-borneol, tocopherol nicotinate, inositol hexanicotinate, cyclandelate, cinnarizine, tolazoline, acetylcholine, verapamil, cepharanthine, gamma-orizanol and the like; astringents such as zinc oxide, tannic acid and the like; antiseborrheic agents such as sulfur, thianthol and the like; and the like.

As examples of vitamins, mention may be made of vitamin As such as vitamin A oil, retinol, retinol acetate, retinol palmitate and the like; vitamin Bs such as vitamin B2s such as riboflavin, riboflavin butyrate, flavin adenine dinucleotide and the like; vitamin B6s such as pyridoxine hydrochloride, pyridoxine dioctanoate, pyridoxine tripalmitate and the like; vitamin B12 and derivatives thereof; vitamin B15 and derivatives thereof, and the like; vitamin Cs such as L-ascorbic acid, L-ascorbyl dipalmitic acid esters, sodium L-ascorbyl 2-sulfate, dipotassium L-ascorbyl phosphoric acid diester and the like; vitamin Ds such as ergocalciferol, cholecalciferol and the like; vitamin Es such as alpha-tocopherol, beta-tocopherol, gamma-tocopherol, dl-alpha-tocopherol acetate, dl-alpha-tocopherol nicotinate, dl-alpha-tocopherol succinate and the like; vitamin H; vitamin P; nicotinic acids such as nicotinic acid, benzyl nicotinate and the like; pantothenic acids such as calcium pantothenate, D-pantothenyl alcohol, pantothenyl ethyl ether, acetyl pantothenyl ethyl ether and the like; and the like.

As examples of amino acids, mention may be made of glycine, valine, leucine, isoleucine, serine, threonine, phenylalanine, arginine, lysine, aspartic acid, glutamate, cystine, cysteine, methionine, tryptophan and the like.

As examples of nucleic acids, mention may be made of deoxyribonucleic acid and the like.

As examples of hormones, mention may be made of estradiol, ethenyl estradiol and the like.

In the cosmetics of the present invention, natural vegetable extract components, seaweed extract components and herbal medicine components can be blended in accordance with the purposes thereof. The aforementioned components can be blended in combination of two or more types thereof.

As detailed examples thereof, mention may be made of, for example, *Angelica keiskei* extract, avocado extract, *Hydrangea serrata* extract, *Althaea officinalis* extract, *Arnica montana* extract, aloe extract, apricot extract, apricot kernel extract, *Gingko biloba* extract, fennel fruit extract, turmeric root extract, oolong tea extract, *Rosa multiflora* extract, *Echinacea angustifolia* leaf extract, *Scutellaria baicalensis* root Extract, *Phellodendron amurense* bark extract, *Coptis rhizome* extract, *Hordeum vulgare* seed extract, *Hypericum perforatum* extract, *Lamium album* extract, *Nasturtium officinale* extract, orange extract, dried sea water solution, seaweed extract, hydrolyzed elastin, hydrolyzed wheat powders, hydrolyzed silk, *Chamomilla recutita* extract, carrot extract, *Artemisia capillaris* flower extract, *Glycyrrhiza glabra* extract, *Hibiscus sabdariffa* extract, *Pyracantha fortuneana* extract, kiwi extract, *Cinchona succirubra* extract, cucumber extract, guanosine, *Gardenia florida* extact, *Sasa veitchii* extract, *Sophora angustifolia* extract, walnut extract, grapefruit extract, *Clematis vitalba* leaf extract, *chlorella* extract, *Morus alba* extract, *Gentiana lutea* extract, black tea extract, yeast extract, burdock extract, fermented rice bran extract, rice germ oil, *Symphytum officinale* leaf extract, collagen, *Vaccinum vitis idaea* extract, *Asiasarum sieboldi* extract, *Bupleurum falcatum* extract, umbilical extract, *Salvia* extract, *Crocus sativus* flower extract, sasa bamboo grass extract, *Crataegus cuneata* fruit extract, *Zanthoxylum piperitum* extract, *Corthellus shiitake* extract, *Rehmannia chinensis* root extract, *Lithospermum erythrorhizone* root extract, *Perilla ocymoides* extract, *Tilia cordata* extract, *Spiraea ulmaria* extract, *Paeonia albiflora* extract, *Acorns calamus* root extract, *Betula alba* extract, *Equisetum arvense* extract, *Hedera helix* extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, soybean seed extract, *Zizyphus jujuba* fruit extract, thyme extract, *Camellia sinensis* leaf extract, *Eugenia caryophyllus* flower extract, *Imperata cylindrica* extract, *Citrus unshiu* peel extract, *Angelica acutiloba* root extract, *Calendula officinalis* extract, *Prunus persica* kernel extract, *Citrus aurantium* peel extract, *Houttuynia cordata* extract, tomato extract, natto extract, carrot extract, garlic extract, *Rosa canina* fruit extract, hibiscus extract, *Ophiopogon japonicus* root extract, *Nelumbo nucifera* extract, parsley extract, honey, *Hamamelis virginiana* extract, *Parietaria officinalis* extract, *Isodon trichocarpus* extract, bisabolol, *Eriobotrya japonica* extract, *Tussilago farfara* flower extract, *Petasites japonicus* extract, *Poria cocos* extract, *Ruscus aculeatus* root extract, grape extract, propolis, *Luffa cylindrica* fruit extract, safflower flower extract, peppermint extract, *Tillia miquellana* extract, *Paeonia suffruticosa* root extract, *Humulus lupulus* extract, *Pinus sylvestris* cone extract, horse chestnut extract, *Lysichiton camtschatcense* extract, *Sapindus mukurossi* peel extract, *Melissa officinalis* leaf extract, peach extract, *Centaurea cyanus* flower extract, *Eucalyptus globulus* leaf extract, *Saxifraga sarementosa* extract, *Citrus junos* extract, *Coix lacryma-jobi* seed extract, *Artemisia princeps* extract, lavender extract, apple extract, lettuce extract, lemon, extract, *Astragalus sinicus* extract, rose extract, rosemary extract, *Roman chamomile* extract, and royal jelly extract. Those which are lipophilic are particularly preferred.

In the cosmetics of the present invention, depending on the purposes thereof, solvents such as light isoparaffins, ethers, LPG, N-methylpyrrolidone, next-generation chlorofluorocarbons, and the like, can be blended in addition to water such as purified water, mineral water and the like.

In addition, in the cosmetic of the present invention, at least one material selected from the group consisting of acrylsilicone dendrimer copolymers, polyamide-modified silicones, alkyl-modified silicone waxes and alkyl-modified silicone resin waxes can be used, in addition to the copolymer of the present invention.

As particularly preferable examples of the acrylsilicone dendrimer copolymers, mention may be made of, for example, a vinyl-based polymer having a carbosiloxane dendrimer structure at the side chain, which is described in Japanese Patent No. 4009382 (Japanese Unexamined Patent Application, First Publication No. 2000-063225). As examples of commercially available products, mention may be made of FA 4001 CM Silicone Acrylate, and FA 4002 ID Silicone Acrylate (manufactured by Dow Corning Toray Co., Ltd.) and the like.

As examples of the polyamide-modified silicones, mention may be made of, for example, siloxane-based polyamides described in U.S. Pat. No. 5,981,680. As examples of commercially available products, mention may be made of 2-8178 Gellant, and 2-8179 Gellant (manufactured by Dow Corning Corporation, in the USA) and the like.

As examples of the alkyl-modified silicone waxes which may be an alkyl-modified silicone in the form of a wax at room temperature, mention may be made of, for example, a methyl(long-chain alkyl)polysiloxane of which both molecular terminals are capped with, trimethylsiloxy groups, a copolymer of a methyl(long-chain alkyl)siloxane and a dimethylpolysiloxane of which both molecular terminals are capped with trimethylsiloxy groups, a both-terminal (long-chain alkyl)-modified dimethylpolysiloxane and the like. As examples of the commercially available products thereof, mention may be made of AMS-C30 Cosmetic Wax, and 2503 Cosmetic Wax (manufactured by Dow Corning Corporation, in the USA) and the like.

As preferable examples of the alkyl-modified silicone resin waxes, mention may be made of, for example, silsesquioxane resin waxes described in Published Japanese Translation No. 2007-532754 of the PCT International Application.

The cosmetics of the present invention can be in the form of liquids, milky lotions, creams, solids, pastes, gels, powders, lamellas, mousses, sprays and the like. As examples of the cosmetics of the present invention, mention may be made of, for example, UV-ray protective products such as sunscreen agents and the like; skin care products such as cosmetic lotions, cosmetic milks, creams, cleansing products, products for use in massaging, cleansing agents and the like; makeup products such as foundations, makeup bases, cheek colors, eye shadows, mascaras, eyeliners, lipsticks and the like; products for use on hair such as shampoos, rinses, treatments and the like; antiperspirant products; deodorant products and the like.

EXAMPLES

Hereinafter, the present invention is described in detail with reference to examples and comparative examples. It should be understood that the present invention is not restricted to the examples. In the following description, "%" and "parts" mean "% by weight" and "parts by weight", respectively.

Example 1

100 g of isopropyl alcohol was placed in a four-necked flask with a volume of 500 mL, equipped with a stirrer, a thermometer and a reflux condenser, and bubbling with a nitrogen gas was carried out to sufficiently deaerate, followed by heating to 80° C. 34 g of methyl methacrylate, 10 g of stearyl methacrylate, 16 g of n-butyl acrylate, 40 g of a carbosiloxane dendrimer monomer represented by the following formula (A):

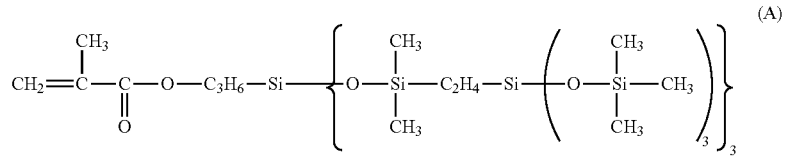

and 1.0 g of 2,2'-azobis-2-methylbutyronitrile (manufactured by Otsuka Pharmaceutical Co., Ltd.) were placed in a dropping funnel, and they were dissolved. The monomer mixture was added dropwise to the flask which was maintained at 80° C., from the dropping funnel over 2 hours under a nitrogen atmosphere. After completion of the dropwise addition, the mixture was heated and stirred for 6 hours under a nitrogen atmosphere. The reaction product after stirring was subjected to analysis of the polymerization addition rate by means of gas chromatography. As a result, the addition rate of polymerization was 97%, and it was confirmed that a vinyl-based polymer was obtained. 250 g of decamethylpentacyclosiloxane was added to the isopropyl alcohol solution of the aforementioned vinyl-based polymer, and subsequently, IPA was removed by distillation at 120° C. Redundant decamethylpentacyclosiloxane and unreacted monomers were removed by distillation under reduced pressure. Thereby, the concentration of the solid content was adjusted to 30% by weight.

Example 2

100 g of isopropyl alcohol was placed in a four-necked flask with a volume of 500 mL, equipped with a stirrer, a thermometer and a reflux condenser, and bubbling with a nitrogen gas was carried out to sufficiently deaerate, followed by heating to 80° C. 27 g of methyl methacrylate, 20 g of stearyl methacrylate, 8 g of n-butyl acrylate, 45 g of a carbosiloxane dendrimer monomer represented by the aforementioned formula (A) and 1.0 g of dimethyl-2,2'-azobis(2-methylpropionate) (manufactured by Wako Pure Chemical Industries, Ltd.) were placed in a dropping funnel, and they were dissolved. The monomer mixture was added dropwise to the flask which was maintained at 80° C. from the dropping funnel over 2 hours under a nitrogen atmosphere. After completion of the dropwise addition, the mixture was heated and stirred for 6 hours under a nitrogen atmosphere. The reaction product after stirring was subjected to analysis of the polymerization addition rate by means of gas chromatography. As a result, the addition rate of polymerization was 98%, and it was confirmed that a vinyl-based polymer was obtained. 250 g of decamethylpentacyclosiloxane was added to the isopropyl alcohol solution of the aforementioned vinyl-based polymer. The reaction mixture was transferred to an autoclave with a volume of 1 L, and 1 g of a sponge nickel catalyst was added thereto to carry out hydrogen substitution. The reaction mixture was heated to 100° C., and hydrogen was fed to 0.8 Mpa, followed by carrying out heating and aging for 6 hours. After the catalyst was removed by filtration, the filtrate was subjected to solvent replacement with decamethylpentacyclosiloxane under heating at 140° C. for 30 minutes by reducing pressure by 10 mmHg. The hydrogenated unreacted monomers were removed. Thereby, the concentration of the solid content was adjusted to 30% by weight.

Example 3

100 g of isopropyl alcohol was placed in a four-necked flask with a volume of 300 mL, equipped with a stirrer, a thermometer and a reflux condenser, and bubbling with a nitrogen gas was carried out to sufficiently deaerate, followed by heating to 80° C. 20 g of methyl methacrylate, 30 g of stearyl methacrylate, 10 g of n-butyl acrylate, 40 g of the carbosiloxane dendrimer monomer represented by the aforementioned formula (A) and 1.0 g of 2,2'-azobis-2-methylbutyronitrile (manufactured by Otsuka Pharmaceutical Co., Ltd.) were placed in a dropping funnel, and they were dissolved. The monomer mixture was added dropwise to the flask which was maintained at 80° C. from the dropping funnel over 2 hours under a nitrogen atmosphere. After completion of the dropwise addition, the mixture was heated and stirred for 6 hours under a nitrogen atmosphere. The reaction product after stirring was subjected to analysis of the polymerization addition rate by means of gas chromatography. As a result, the addition rate of polymerization was 97%, and it was confirmed that a vinyl-based polymer was obtained. 175 g of isododecane was added to the isopropyl alcohol solution of the aforementioned vinyl-based polymer. Subsequently, IPA was removed by distillation at 120° C. Redundant isododecane and unreacted monomers were removed by distillation under reduced pressure. Thereby, the concentration of the solid content was adjusted to 40% by weight.

Example 4

100 g of isopropyl alcohol was placed in a four-necked flask with a volume of 300 mL, equipped with a stirrer, a thermometer and a reflux condenser, and bubbling with a nitrogen gas was carried out to sufficiently deaerate, followed by heating to 80° C. 30 g of trifluoroethyl methacrylate, 15 g of stearyl acrylate, 5 g of n-butyl acrylate, 50 g of the carbosiloxane dendrimer monomer represented by the aforementioned formula (A) and 1.0 g of 2,2'-azobis-2-methylbutyronitrile (manufactured by Otsuka Pharmaceutical Co., Ltd.) were placed in a dropping funnel, and they were dissolved. The monomer mixture was added dropwise to the flask which was maintained at 80° C. from the dropping funnel over 2 hours under a nitrogen atmosphere. After completion of the dropwise addition, the mixture was heated and stirred for 6 hours under a nitrogen atmosphere. The reaction product after stirring was subjected to analysis of the polymerization addition rate by means of gas chromatography. As a result, the addition rate of polymerization was 97%, and it was confirmed that a vinyl-based polymer was obtained. 250 g of dimethylpolysiloxane (2 cs) was added to the isopropyl alcohol solution of the aforementioned vinyl-based polymer. Subsequently, IPA was removed by distillation at 120° C. Redundant dimethylpolysiloxane (2 cs) and unreacted monomers were removed by distillation under reduced pressure. Thereby, the concentration of the solid content was adjusted to 30% by weight.

Comparative Example 1

100 g of isopropyl alcohol was placed in a four-necked flask with a volume of 300 mL, equipped with a stirrer, a thermometer and a reflux condenser, and bubbling with a nitrogen gas was carried out to sufficiently deaerate, followed by heating to 80° C. 5 g of methyl methacrylate, 55 g of stearyl methacrylate, 40 g of the carbosiloxane dendrimer monomer represented by the aforementioned formula (A) and 1.0 g of 2,2'-azobis-2-methylbutyronitrile (manufactured by Otsuka Pharmaceutical Co., Ltd.) were placed in a dropping funnel, and they were dissolved. The monomer mixture was added dropwise to the flask which was maintained at 80° C. from the dropping funnel over 2 hours under a nitrogen atmosphere. After completion of the dropwise addition, the mixture was heated and stirred for 6 hours under a nitrogen atmosphere. The reaction product after stirring was subjected to analysis of the polymerization addition rate by means of gas chromatography. As a result, the addition rate of polymerization was 97%, and it was confirmed that a vinyl-based polymer was obtained. The isopropyl alcohol solution of the aforementioned vinyl-based polymer was heated at 140° C. under reducing pressure by 10 mmHg for 30 minutes to remove isopropyl alcohol and unreacted monomers.

Comparative Example 2

100 g of isopropyl alcohol was placed in a four-necked flask with a volume of 500 mL, equipped with a stirrer, a thermometer and a reflux condenser, and bubbling with a nitrogen gas was carried out to sufficiently deaerate, followed by heating to 80° C. 50 g of methyl methacrylate, 10 g of n-butyl acrylate, 40 g of the carbosiloxane dendrimer monomer represented by the aforementioned formula (A) and 1.0 g of 2,2'-azobis-2-methylbutyronitrile (manufactured by Otsuka Pharmaceutical Co., Ltd.) were placed in a dropping funnel, and they were dissolved. The monomer mixture was added dropwise to the flask which was maintained at 80° C. from the dropping funnel over 2 hours under a nitrogen atmosphere. After completion of the dropwise addition, the mixture was heated and stirred for 6 hours under a nitrogen atmosphere. The reaction product after stirring was subjected to analysis of the polymerization addition rata by means of gas chromatography. As a result, the addition rate of polymerization was 97%, and it was confirmed that a vinyl-based polymer was obtained. 250 g of decamethylpentacyclosiloxane was added to the isopropyl alcohol solution of the aforementioned vinyl-based polymer. Subsequently, IPA was removed by distillation at 120° C. Redundant decamethylpentacyclosiloxane and unreacted monomers were removed by distillation under reduced pressure. Thereby, the concentration of the solid content was adjusted to 30% by weight.

Comparative Example 3

100 g of isopropyl alcohol was placed in a four-necked flask with a volume of 500 mL, equipped with a stirrer, a thermometer and a reflux condenser, and bubbling with a nitrogen gas was carried out to sufficiently deaerate, followed by heating to 80° C. 34 g of methyl methacrylate, 10 g of stearyl methacrylate, 16 g of n-butyl acrylate, 40 g of a one-terminal, radical-polymerizable dimethylpolysiloxane (pentacosamer) represented by the following formula:

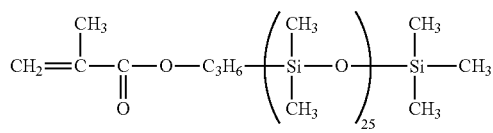

and 1.0 g of 2,2'-azobis-2-methylbutyronitrile (manufactured by Otsuka Pharmaceutical Co., Ltd.) were placed in a dropping funnel, and they were dissolved. The monomer mixture was added dropwise to the flask which was maintained at 80° C. from the dropping funnel over 2 hours under a nitrogen atmosphere. After completion of the dropwise addition, the mixture was heated and stirred for 6 hours under a nitrogen atmosphere. The reaction product after stirring was subjected to analysis of the polymerization addition rate by means of gas chromatography. As a result, the addition rate of polymerization was 97%, and it was confirmed that a vinyl-based polymer was obtained. 250 g of decamethylpentacyclosiloxane was added to the isopropyl alcohol solution of the aforementioned vinyl-based polymer. Subsequently, IPA was removed by distillation at 120° C. Redundant decamethylpentacyclosiloxane and unreacted monomers were removed by distillation under reduced pressure. Thereby, the concentration of the solid content was adjusted to 30% by weight.

Evaluation

Evaluation was carried out with respect to various properties of water resistance (water repellency), sebum resistance, glass transition temperature, tactile sensation and glossiness of the vinyl-based copolymers of Examples 1 to 4 and Comparative Examples 1 to 3. The results are shown in Table 1.

Water Resistance (Water Repellency)

The vinyl-based copolymer was applied on a glass plate, and subsequently, the solvent was removed by drying at room temperature. Thereby, a coating film of the vinyl-based polymer was obtained. A water droplet was mounted on the surface of the aforementioned coating film, and the contact angle with respect to water was measured. As the measurement apparatus, an automatic contact angle meter (manufactured by Kyowa Interface Science Co., Ltd.) was used.

Sebum Resistance

The vinyl-based copolymer was applied on a glass plate, and subsequently, the solvent was removed by drying at room temperature. Thereby, a coating film of the vinyl-based polymer was obtained. A squalane droplet was mounted on the surface of the aforementioned coating film, and the contact angle with respect to squalane droplet was measured. As the measurement apparatus, an automatic contact angle meter (manufactured by Kyowa Interface Science Co., Ltd.) was used. A contact angle of 50° or more is indicated by OO, a contact angle of more than 40°, but less than 50° is indicated by O, and a contact angle of 40° or less is indicated by Δ.

Glass Transition Temperature

The glass transition temperature of the vinyl-based copolymer was measured by means of a differential scanning calorimeter (DSC).

Tactile Sensation

The vinyl-based copolymer was applied on a glass plate, and subsequently, the solvent was removed by drying at room temperature. Thereby, a coating film of the vinyl-based polymer was obtained. The tactile sensation of the surface of the aforementioned coating film was measured by contacting with the fingers.

Glossiness

The vinyl-based copolymer was applied on a light-nonreflecting PET plate, and subsequently, the solvent was removed by drying at room temperature. Thereby, a coating film of the vinyl-based polymer was obtained. The glossiness of the surface of the coating film was measured by means of a glossmeter (60 degrees). A glossiness of 75 degrees or more is indicated as OO, a glossiness of more than 60 degrees, but less than 75 degrees is indicated as O and a glossiness of 60 degree's or less is indicated as Δ.

Miscibility with an Organic Wax

The copolymer synthesized in each of the aforementioned Examples and Comparative Examples, in the form of a partially IPA solution, was transferred to another flask. The IPA was removed by distillation, and thereby, a solid copolymer was obtained. As the organic waxes, a commercially available beeswax and a commercially available candelilla wax were selected, and each of the copolymers was mixed therewith in accordance with the following composition and heated at 80° C. The miscibility was evaluated based on the outer appearance at 80° C.

Organic wax=one part
Copolymer=one part
Isodecyl neopentanoate=2.5 parts

TABLE 1

|  | Example 1 | Example 2 | Example 3 | Example 4 | Comparative Example 1 | Comparative Example 2 | Comparative Example 3 |
|---|---|---|---|---|---|---|---|
| Methyl methacrylate | 34 | 27 | 20 | — | 5 | 50 | 34 |
| Stearyl methacrylate | 10 | 20 | 30 | — | 55 | — | 10 |
| Stearyl acrylate | — | — | — | 15 | — | — | — |
| Trifluoroethyl methacrylate | — | — | — | 30 | — | — | — |
| n-butyl acrylate | 16 | 8 | 10 | 5 | — | 10 | 16 |

TABLE 1-continued

|  | Example 1 | Example 2 | Example 3 | Example 4 | Comparative Example 1 | Comparative Example 2 | Comparative Example 3 |
|---|---|---|---|---|---|---|---|
| Carbosiloxane dendrimer monomer | 40 | 45 | 40 | 50 | 40 | 40 | — |
| One-terminal radical-polymerizable dimethylpolysiloxane | — | — | — | — | — | — | 40 |
| Glass transition temperature | 31 | 46 | 35 | 38 | 43 | 60 | 31 |
| Water repellency | 105.3 | 102.2 | 97.6 | 103.8 | 111.3 | 95 | 95 |
| Sebum resistance | ⊚ | ⊚ | ⊚ | ⊚ | Δ | ⊚ | Δ |
| Tactile sensation | good | good | good | good | good | good | presence of stickiness |
| Glossiness | ⊚ | ⊚ | ⊚ | ⊚ | Δ | ○ | ○ |
| Miscibility with organic wax (beeswax) | dissolved | dissolved | dissolved | dissolved | dissolved | separated | separated |
| Miscibility with organic wax (candelilla wax) | dissolved | dissolved | dissolved | dissolved | dissolved | separated | separated |

Example 5

100 g of isopropyl alcohol was placed in a four-necked flask with a volume of 300 mL, equipped with a stirrer, a thermometer and a reflux condenser, and bubbling with a nitrogen gas was carried out to sufficiently deaerate, followed by heating to 80° C. 30 g of methyl methacrylate, 20 g of behenyl acrylate, 10 g of n-butyl acrylate, 40 g of the carbosiloxane dendrimer monomer represented by the aforementioned formula (A) and 1.0 g of 2,2'-azobis-2-methyl-butyronitrile (manufactured by Otsuka Pharmaceutical Co., Ltd.) were placed in a dropping funnel, and they were dissolved. The monomer mixture was added dropwise to the flask which was maintained at 80° C. from the dropping funnel over 2 hours under a nitrogen atmosphere. After completion of the dropwise addition, the mixture was heated and stirred for 6 hours under a nitrogen atmosphere. The reaction product after stirring was subjected to analysis of the polymerization addition rate by means of gas chromatography. As a result, the addition rate of polymerization was 97%, and it was confirmed that a vinyl-based polymer was obtained. 250 g of isodecyl neopentanoate was added to the isopropyl alcohol solution of the aforementioned vinyl-based polymer. Subsequently, IPA was removed by distillation at 120° C. Redundant isodecyl neopentanoate and unreacted monomers were removed by distillation under reduced pressure. Thereby, the concentration of the solid content was adjusted to 30% by weight.

The water repellency and tactile sensation of the obtained vinyl-based copolymer was evaluated in the same manner as described above. The water repellency was "101", and tactile sensation was good.

Hereinafter, composition examples and preparation examples of the cosmetics of the present invention are described in detail.

Composition Example 1

Sunscreen (W/O) Double Layer Shaking Type

| (Components) | (part(s)) |
|---|---|
| Phase A | |
| (1) Octyl methoxycinnamate | 10 |
| (2) Titanium oxide, cyclopentasiloxane (sample TiO₂ 30%) | 1 |
| (3) Zinc oxide, cyclopentasiloxane (sample ZnO 50%) | 32 |
| (4) Cyclopentasiloxane | 20.2 |
| (5) Dimethicone crosspolymer (Note 1) | 3 |
| (6) Vinyl-based polymer obtained in Example 2 | 3.3 |
| (7) Phenoxyethanol | 0.9 |
| (8) Ethanol | 5 |
| Phase B | |
| (9) BG | 3 |
| (10) Water | 21.6 |

(Note 1):
DC9045 manufactured by Dow Corning Corporation

Preparation Method

1. Components 4 and 5 are uniformly mixed and dissolved.
2. Components 7 and 8 are uniformly mixed and dissolved.
3. Components 9 and 10 are uniformly mixed and dissolved.
4. Components 1, 2, 3 and 6, as well as the mixture of components 7 and 8 obtained in step 2 are added to the mixture of components 4 and 5 obtained in step 1, and the mixture is stirred.
5. While phase A obtained in step 4 is stirred at 1,500 rpm, phase B obtained in step 3 is added to phase A over 30 seconds.
6. After phase B is added, the mixture is stirred for 5 minutes.

Composition Example 2

Sunscreen (W/O) Cream

| (Components) | (part(s)) |
|---|---|
| Phase A | |
| (1) Octyl methoxycinnamate | 7.5 |
| (2) Cyclopentasiloxane | 5 |
| (3) Vinyl-based polymer obtained in Example 3 | 3 |
| (4) Dimethicone (6 cs) | 1 |

-continued

| | (Components) | (part(s)) |
|---|---|---|
| (5) | Isononyl isononanoate | 1 |
| (6) | Cyclopentasiloxane, dimethicone crosspolymer (Note 1) | 3 |
| (7) | Polysilicone 13 (Note 2) | 2 |
| (8) | Zinc oxide, cyclopentasiloxane (slurry concentration = 50%) | 10 |
| (9) | Cyclopentasiloxane, titanium oxide (slurry concentration = 30%) | 2 |
| | Phase B | |
| (10) | Sodium chloride | 1 |
| (11) | Panthenol | 0.5 |
| (12) | Purified water | 61.95 |
| (13) | Glycerol | 2 |
| (14) | Preservatives | 0.05 |

(Note 1):
DC9040 manufactured by Dow Corning Corporation
(Note 2):
FZ-2233 manufactured by Dow Corning Toray Co., Ltd.

Preparation Method
1. Components 2 and 6 are stirred by means of a disper.
2. Components 1, 3, 4, 5, 7, 8 and 9 are added to the mixture obtained in step 1, and the mixture is uniformly mixed.
3. Components 10 to 14 are uniformly mixed.
4. While phase A obtained in step 2 is stirred at 3,000 rpm, phase B obtained in step 3 is added to phase A over 30 seconds.
5. After phase B is added, the mixture is stirred for 3 minutes, for 3 minutes, and for 4 minutes.

Composition Example 3

Sunscreen (O/W) Cream

| | (Components) | (part(s)) |
|---|---|---|
| | Phase A | |
| (1) | PEG/PPG-30/10 dimethicone, dimethicone and the like (Note 1) | 10 |
| (2) | Sodium tri(POE)lauryl ether phosphate | 0.05 |
| (3) | Diethylaminohydroxybenzoyl and hexyl benzoate | 6 |
| (4) | Ethylhexyl methoxycinnamate | 2 |
| (5) | Vinyl-based polymer obtained in Example 1 | 3 |
| (6) | Dimethicone 6 cs | 1 |
| (7) | Bis(hydroxyethoxypropyl)dimethicone (Note 2) | 1 |
| (8) | Phenyltrimethicone | 2 |
| | Phase B | |
| (9) | Carbomer (2% aqueous solution) | 22.5 |
| (10) | Purified water | 27 |
| (11) | Sodium hydroxide (1% aqueous solution) | 10.5 |
| | Phase C | |
| (12) | Polyoxypropylene methylglucoside | 0.4 |
| (13) | Ethanol | 2 |
| (14) | BG | 5 |
| (15) | Glycerol | 5 |
| (16) | Preservatives | 0.05 |
| | Phase D | |
| (17) | (Dimethicone/vinyldimethicone) crosspolymer (Note 3) | 2.5 |

(Note 1):
FB-2540 manufactured by Dow Corning Toray Co., Ltd.
(Note 2):
DC-5562 manufactured by Dow Corning Corporation
(Note 3):
BY29-129 manufactured by Dow Corning Toray Co., Ltd.

Preparation Method
1. Components 9 to 11 are uniformly mixed.
2. Components 12 to 16 are uniformly mixed.
3. Components 1, 3 and 4 are mixed and further mixed with components 2, 5, 6, 7 and 8.
4. While Phase B obtained in step 1 is stirred at 3,000 rpm, phase A obtained in step 3 is added to phase B over 30 seconds.
5. After adding phase A, the mixture is stirred for 3 minutes and for 5 minutes.
6. While the mixture obtained in step 5 is stirred at 2,000 rpm, phase C obtained in step 2 is added to the aforementioned mixture over 30 seconds.
7. After phase C is added, the mixture is stirred for 2 minutes and for 4 minutes.
8. In addition, component 17 is added thereto, and the mixture is stirred for one minute at 1,000 rpm.

Composition Example 4

Liquid Foundation

| | (Components) | (part(s)) |
|---|---|---|
| | Phase A | |
| (1) | Dextrin palmitate | 2.1 |
| (2) | Glyceryl tricaprylate/tricaprate | 5 |
| (3) | PEG/PPG-18/18 dimethicone (Note 1) | 10 |
| (4) | PEG-12 dimethicone (Note 2) | 1.9 |
| | Phase B | |
| (6) | Cyclopentasiloxane | 20 |
| (7) | Silicone-treated iron oxide | 3.5 |
| (8) | Silicone-treated mica | 3.5 |
| (9) | Vinyl-based polymer obtained in Example 5 | 3 |
| (10) | Dimethicone crosspolymer (Note 3) | 2 |
| | Phase C | |
| (11) | Purified water | 48 |
| (12) | Sodium chloride | 1 |

(Note 1):
DC5225C manufactured by Dow Corning Corporation
(Note 2):
DC193C manufactured by Dow Corning Corporation
(Note 3):
DC9040 manufactured by Dow Corning Corporation Preparation Method
1. Components 1 to 4 are mixed at 80 to 90° C. to completely dissolve them, and the solution is cooled to 50° C.
2. Components 6 to 10 are uniformly mixed.
3. Phase A obtained in step 1 and phase B obtained in step 2 are mixed.
4. Components 11 and 12 are added to the mixture obtained in step 3 over 30 seconds.
5. After adding components 11 and 12, the mixture is stirred for 3 minutes, for 3 minutes, and for 4 minutes.

Composition Example 5

Liquid Foundation (O/W)

| (Components) | (part(s)) |
|---|---|
| Phase A | |
| (1) Stearic acid | 3 |
| (2) Glyceryl stearate/stearyl PEG-100 | 2 |
| (3) Glyceryl tricaprylate/glycerol tricaprate | 3 |
| (4) Heavy liquid paraffin | 3.4 |
| (5) Dimethicone (6 cs) | 2.3 |
| (6) Vinyl-based polymer obtained in Example 4 | 6.7 |
| Phase B | |
| (7) 1,3-butylene glycol | 8 |
| (8) Titanium oxide | 9.5 |
| (9) Red iron oxide | 0.35 |
| (10) Black iron oxide | 0.1 |
| (11) Yellow iron oxide | 1.5 |
| (12) Talc | 1 |
| (13) Preservatives | 0.3 |
| Phase C | |
| (14) Purified water | 57.95 |
| Phase D | |
| (15) Triethanolamine | 0.9 |

Preparation Method

1. Components 7 to 13 are mixed.
2. Components 1 to 6 are mixed at 80 to 90° C. to completely dissolve them, and the solution is cooled to 50° C.
3. Component 14 is heated to 85° C.
4. Phase B obtained in step 1 is added to phase C obtained in step 3 over 30 seconds, and the mixture is stirred at 3,000 rpm.
5. The revolutions per minute are reduced to 1,000 rpm, and the mixture of phase B obtained in step 1 is added thereto.
6. The mixture is stirred for 5 minutes.
7. Component 15 is added thereto, and the pH is adjusted to 6 to 6.5.

Composition Example 6

Powder Foundation

| (Components) | (part(s)) |
|---|---|
| (1) Talc | remainder |
| (2) Mica | 3 |
| (3) Dimethicone/vinyldimethicone cross polymer/silica (Note 1) | 1 |
| (4) Silicone-treated titanium oxide | 9 |
| (5) Silicone-treated fine powder of zinc oxide | 5 |
| (6) Silicone-treated fine powder of titanium oxide | 5 |
| (7) Red iron oxide | 0.2 |
| (8) Yellow iron oxide | 1.4 |
| (9) Black iron oxide | 0.3 |
| (10) Platy barium sulfate (average particle size = 30 μm) | 7.5 |
| (11) Polymethyl methacrylate | 7.5 |
| (12) Paraben | 0.2 |
| (13) Phenylmethylsilicone | 5 |
| (14) Vinyl-based polymer obtained in Example 3 | 2 |
| (15) Ethylhexyl methoxycinnamate | 1 |
| (16) Diisostearyl malate | 3 |
| (17) Dimethylpolysiloxane (350 cSt) | 2 |
| (18) Glycerol | 0.2 |
| (19) Perfume | q.s. |

(Note 1):
9701 Cosmetic Powder manufactured by Dow Corning Toray Co., Ltd.

Preparation Method

1. Components 11 to 18 are mixed and dissolved.
2. Components 1 to 10 are mixed.
3. The mixture obtained in step 2 is added to the mixture obtained in step 1, and the mixture is mixed and kneaded, and then pulverized.
4. The pulverized product obtained in step 3 is subjected to press molding in a metal mold, and thereby, a solid powder foundation is obtained.

Composition Example 7

Lipstick

| (Components) | (part(s)) |
|---|---|
| Phase A | |
| (1) PEG/PPG-18/18 dimethicone (Note 1) | 4.2 |
| (2) Alkyl-modified silicone (Note 2) | 2 |
| (3) Red iron oxide (69% in DC 5562 Carbinol Fluid) | 1 |
| (4) Red No. 7 (42% in DC 5562 Carbinol Fluid) | 10 |
| (5) Yellow iron oxide (55% in DC 5562 Carbinol Fluid) | 1 |
| (6) Malic acid diester | 1 |
| Phase B | |
| (7) Organic bentonite (Bentone 38) | 2 |
| Phase C | |
| (8) Dimethicone (2 cs) | 18.5 |
| (9) Dimethicone with a high degree of polymerization (Note 3) | 2 |
| (10) Vinyl-based polymer obtained in Example 5 | 19 |
| (11) Trimethylsiloxysilicic acid | 2 |
| Phase D | |
| (12) Silylated silica | 1 |
| Phase E | |
| (13) Alkylsilane-treated mica | 9 |
| Phase F | |
| (14) Carbomer (2% aqueous solution) | 20 |
| (15) Preservatives | q.s. |
| (16) Purified water | 4.8 |
| Phase G | |
| (17) Perfume | |

(Note 1):
DC5225C manufactured by Dow Corning Corporation
(Note 2):
AMS-C30 COSMETIC WAX manufactured by Dow Corning Corporation
(Note 3):
BY11-040 manufactured by Dow Corning Toray Co., Ltd.

Preparation Method

1. Components 1 to 6 are mixed at 80° C.
2. Component 7 is added to phase A obtained in step 1, and the mixture is stirred.
3. Components 8 to 13 are further added thereto, and mixed.
4. Components 14 to 16 are further added thereto, and mixed at 70° C.

5. The mixture of phase A and phase B obtained in step 2 and the mixture of phases C, D and E obtained in step 3 are mixed at 1,000 rpm, and phase F obtained in step 4 is added thereto over 30 seconds, followed by further stirring for 3 minutes.
6. Component 17 is further added thereto, and mixed.

Composition Example 8

Transparent Lip Gloss

| | (Components) | (part(s)) |
|---|---|---|
| (1) | Polyamide-modified silicone (2-8178) | 16.5 |
| (2) | Decamethylpentacyclosiloxane | 33 |
| (3) | Vinyl-based polymer obtained in Example 2 | 3 |
| (4) | Isopropyl myristate | 20 |
| (5) | Glyceryl tricaprylate/tricaprate | 21.8 |
| (6) | Trimethylpentaphenyltrisiloxane | 5.5 |
| (7) | Pigments | 0.2 |

Preparation Method
1. All components are mixed at 100° C.
2. The mixture is poured into a metal mold.
3. The mixture is allowed to stand for one hour.

Composition Example 9

Mascara

| | (Components) | (part(s)) |
|---|---|---|
| Phase A | | |
| (1) | Beeswax | 10 |
| (2) | Ozokerite | 7 |
| (3) | Carnauba wax | 3 |
| (4) | Stearic acid | 5 |
| (5) | Glyceryl stearate | 5 |
| Phase B | | |
| (6) | Water | 35.5 |
| (7) | Propylene glycol | 5 |
| (8) | Triethanolamine | 1.5 |
| Phase C | | |
| (9) | Black iron oxide | 10 |
| Phase D | | |
| (10) | Vinyl-based polymer obtained in Example 4 | 10 |
| (11) | Isododecane | 8 |

Preparation Method
1. Components 1 to 5 are mixed and heated to 85° C.
2. Components 6 to 8 are mixed and heated to 80° C.
3. While phase B obtained in step 2 is stirred at 1,000 rpm, phase A obtained in step 1 is added to phase B over 30 seconds.
4. Component 9 is added to the solution obtained in step 3, and the mixture is stirred for 2 minutes.
5. The mixture is cooled to 50° C.
6. Components 10 and 11 are added to the mixture obtained in step 5, and the mixture is stirred.

Composition Example 10

Eye Shadow

| | (Components) | (part(s)) |
|---|---|---|
| (1) | Talc | 20 |
| (2) | Mica | 20 |
| (3) | Sericite | 10 |
| (4) | Nylon (trademark) powder | 5 |
| (5) | Colored pigments | 10 |
| (6) | Titanium mica | 20 |
| (7) | Dimethylpolysiloxane | 5 |
| (8) | Vaseline | 2 |
| (9) | Vinyl-based polymer obtained in Example 3 | 1 |
| (10) | Liquid paraffin | remainder |

Preparation Method
Components 1 to 10 are mixed, and the mixture is subjected to pulverization, followed by being pressed.

The invention claimed is:
1. A copolymer of at least,
(A) an unsaturated monomer having a carbosiloxane dendrimer structure represented by the following formula (1):

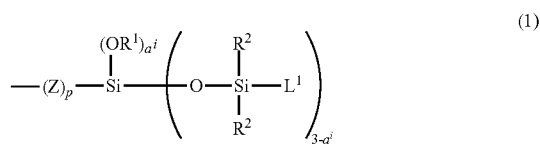

wherein
Z is a divalent organic group;
p is 0 or 1;
each of $R^1$ and $R^2$ independently represents an alkyl group, an aryl group or an aralkyl group, having 1 to 10 carbon atoms; and
$L^1$ is a silylalkyl group, in the case of i=1, represented by the following formula (2):

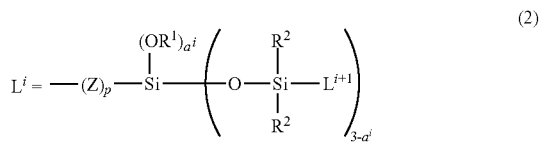

wherein
Z and p are the same as defined above;
$R^1$ and $R^2$ are the same as defined above;
i is an integer ranging from 1 to 10, which specifies the total number of generations of said silylalkyl group;
$L^{i+1}$ is a group selected from the group consisting of a hydrogen atom, alkyl, aryl and aralkyl groups, having 1 to 10 carbon atoms and said silylalkyl group, with the proviso that in the case of i =c, in which c is an integer ranging from 1 to 10, and specifies generation of said silylalkyl group, $L^{i+1}$ is a hydrogen atom, or an alkyl, aryl or aralkyl group, having 1 to 10 carbon atoms; and in the case of i<c, $L^{i+1}$ is said silylalkyl group; and
$a^i$ is an integer ranging from 0 to 3, and
(B) a ($C_{14-22}$ alkyl) (meth)acrylate, and (C) at least two unsaturated monomers having no long-chain alkyl group with 14 to 22 carbon atoms, in addition to components (A) and (B), wherein the copolymer is obtained by copolymerizing said unsaturated monomer having the carbosiloxane dendrimer structure (A), said ($C_{14-22}$) alkyl) (meth) acrylate (B), and said at least two unsaturated monomers having no long-chain alkyl groups with 14 to 22 carbon atoms (C) in a weight ratio satisfying conditions of {(weight of component (A))/(weight of all the monomers)}:{(weight of component (B))/(weight of all the monomers)}:{(weight of component (C))/(weight of all the monomers)} in the range of (0.4 to 0.9):(0.05 to 0.4):(0.05 to 0.65).

2. The copolymer according to claim 1, wherein said unsaturated monomer having the carbosiloxane dendrimer structure (A) has a group selected from the group consisting of an acryl or methacryl group-containing organic group represented by the following general formula:

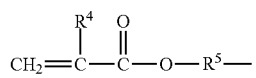

wherein $R^4$ is a hydrogen atom or a methyl group; and $R^5$ is an alkylene group having 1 to 10 carbon atoms, or

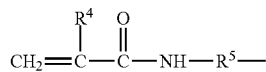

wherein $R^4$ and $R^5$ are the same as defined above, an alkenylaryl group-containing organic group represented by the following general formula:

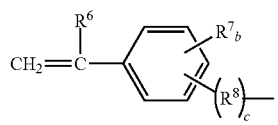

wherein $R^6$ is a hydrogen atom or a methyl group; $R^7$ is an alkyl group having 1 to 10 carbon atoms; $R^8$ is an alkylene group having 1 to 10 carbon atoms; b is an integer ranging from 0 to 4; and c is 0 or 1, and an alkenyl group having 2 to 10 carbon atoms.

3. A copolymer composition comprising the copolymer as recited in claim 1, in an amount of 100 parts by weight; and at least one oil agent, in an amount of 5 to 1,000 parts by weight.

4. The copolymer composition according to claim 3, wherein said oil agent is a liquid at 5 to 100° C., and is at least one selected from silicone oils, hydrocarbon oils and fatty acid ester oils.

5. A cosmetic raw material comprising the copolymer composition as recited in claim 3.

6. A cosmetic comprising the copolymer as recited in claim 1.

7. A cosmetic comprising the copolymer composition as recited in claim 3.

8. The cosmetic according to claim 6, further comprising at least one oil agent.

9. The cosmetic according to claim 8, wherein said oil agent is a silicone oil.

10. The cosmetic according to claim 9, wherein said silicone oil is a hydrophobic silicone oil having a viscosity at 25° C. ranging from 0.65 to 100,000 mm²/s.

11. The cosmetic according to claim 9, wherein said silicone oil is an organopolysiloxane represented by the following formula (3) or (4):

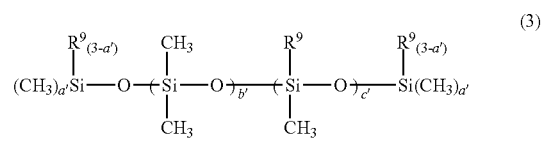

wherein $R^9$ is a hydrogen atom, a hydroxyl group or a group selected from monovalent non-substituted or fluorine- or amino-substituted $C_{1-30}$ alkyl groups, aryl groups, alkoxy groups and groups represented by $(CH_3)_3SiO\{(CH_3)_2SiO\}_lSi(CH_3)_2CH_2CH_2$—, wherein l is an integer ranging from 0 to 1,000;

a' is an integer ranging from 0 to 3;

b' is an integer ranging from 0 to 1,000; and c' is an integer ranging from 0 to 1,000, with the proviso that $1 \leq b'+c' \leq 2,000$,

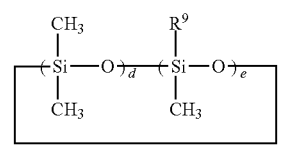

wherein $R^9$ is the same as defined above;

d is an integer ranging from 0 to 8; and e is an integer ranging from 0 to 8, with the proviso that $3 \leq d+e \leq 8$.

12. The cosmetic according to claim 6, further comprising at least one surfactant selected from the group consisting of anionic surfactants, cationic surfactants, nonionic surfactants, amphoteric surfactants and semi-polar surfactants.

13. The cosmetic according to claim 6, further comprising at least one powder and/or at least one coloring agent.

14. The cosmetic according to claim 13, wherein said powder is selected from the group consisting of inorganic pigment powders, organic pigment powders and resin powders, having an average particle size ranging from 1 nm to 20 μm.

15. The cosmetic according to claim 13, wherein at least one part of said powder and/or coloring agent is subjected to a hydrophobic treatment.

16. The cosmetic according to claim 6, further comprising at least one selected from the group consisting of water-soluble polymers, oil-soluble gelling agents and organo-modified clay minerals.

17. The cosmetic according to claim 6, further comprising at least one selected from the group consisting of silicone resins, silicone elastomers and organo-modified silicones.

18. The cosmetic according to claim 6, further comprising at least one UV-ray protective component.

19. A skin care product, a hair product, an antiperspirant product, a deodorant product, a makeup product or a UV-ray protective product comprising the cosmetic as recited in claim 6.

20. The copolymer according to claim 1, wherein at least one of said at least two unsaturated monomers having no long-chain alkyl group with 14 to 22 carbon atoms (C) is methyl methacrylate or n-butyl acrylate.

* * * * *